US009850286B2

(12) United States Patent
Gompels et al.

(10) Patent No.: US 9,850,286 B2
(45) Date of Patent: *Dec. 26, 2017

(54) CYTOKINE

(71) Applicant: LONDON SCHOOL OF HYGIENE AND TROPICAL MEDICINE, London (GB)

(72) Inventors: Ursula Gompels, London (GB); David Dewin, Glasgow (GB); Julie Catusse, Meylan (GB)

(73) Assignee: London School of Hygiene and Tropical Medicine, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/498,317

(22) Filed: Sep. 26, 2014

(65) Prior Publication Data
US 2015/0152141 A1 Jun. 4, 2015

Related U.S. Application Data

(63) Continuation of application No. 11/915,524, filed as application No. PCT/GB2006/050121 on May 25, 2006, now Pat. No. 8,940,686.

(30) Foreign Application Priority Data

May 25, 2005 (GB) .................................. 0510559.8

(51) Int. Cl.
C07K 14/52 (2006.01)
C12N 5/10 (2006.01)
C12N 15/63 (2006.01)
C07K 14/005 (2006.01)
A61K 39/245 (2006.01)
C12N 7/00 (2006.01)
A61K 38/00 (2006.01)
A61K 39/00 (2006.01)

(52) U.S. Cl.
CPC .......... *C07K 14/005* (2013.01); *A61K 39/245* (2013.01); *C07K 14/523* (2013.01); *C12N 7/00* (2013.01); *A61K 38/00* (2013.01); *A61K 2039/53* (2013.01); *C12N 2710/16034* (2013.01); *G01N 2333/521* (2013.01); *G01N 2500/00* (2013.01)

(58) Field of Classification Search
None
See application file for complete search history.

(56) References Cited

U.S. PATENT DOCUMENTS 7,820,436 B2 * 10/2010 Mori et al. .................. 435/320.1
8,940,686 B2 * 1/2015 Gompels et al. ............ 514/1.7

OTHER PUBLICATIONS

Agrawal et al., Multiple Determinants are Involved in HIV Coreceptor use as Demonstrated by CCR4/CCL22 Interaction in Peripheral Blood Mononuclear Cells (PBMCs), Journal of Leukocyte Biology, 72:1063-1074, 2002.
Akhyani et al., Tissue Distribution and Variant Characterization of Human Herpesvirus (HHV)-6: Increased Prevalence of HHV-6A in Patients with Multiple Sclerosis, The Journal of Infectious Diseases, 182:1321-1325, 2000.
Akter et al., Two Novel Spliced Genes in Human Cytomegalovirus, Journal of General Virology, 84:1117-1122, 2003.
Alvarez-Lafuente et al., Relapsing-Remitting Multiple Sclerosis and Human Herpesvirus 6 Active Infection, Archives of Neurology, 61:1523-1527, 2004.
Biragyn et al., Mediators of Innate Immunity That Target Immature, But Not Mature, Dendritic Cells Induce Antitumor Immunity When Genetically Fused With Nonimmunogenic Tumor Antigens, The Journal of Immunology, 167:6644-6653, 2001.
Biragyn et al., Chemokine Receptor-Mediated Delivery Directs Self-Tumor Antigen Efficiently into the Class II Processing Pathway In Vitro and Induces Protective Immunity In Vivo, Blood, 104:1961-1969, 2004.
Bishop et al., CC Chemokine Ligand 1 Promotes Recruitment of Eosinophils But Not Th2 Cells During the Development of Allergic Airways Disease, The Journal of Immunology, 170:4810-4817, 2003.
Boshoff et al., Angiogenic and HIV-Inhibitory Functions of KSHV-Encoded Chemokines, Science, 278:290-294, 1997.
Broxmeyer et al., Effects of CC, CXC, C, and CX3C Chemokines on Proliferation of Myeloid Progenitor Cells, and Insights into SDF-1-Induced Chemotaxis of Progenitors, Annuals of New York Academy of Sciences, 872:142-162, 1999 (Abstract only).
Carrigan et al., Letter to the Editor regarding Bone Marrow Suppression by Human Herpesvirus-6: Comparison of the A and B Variants of the Virus, Blood, 86:835-836, 1995.
Clapham and McKnight, HIV-1 Receptors and Cell Tropism, British Medical Bulletin, 58:43-59, 2001.
Clapham and McKnight, Cell Surface Receptors, Virus Entry and Tropism of Primate Lentiviruses, Journal of General Virology 83:1809-1829, 2002.
Corbellino, M, et al., Disseminated Human Herpesvirus 6 Infection in AIDS, The Lancet, 342:1242, 1993.
Crittenden et al., Expression of Inflammatory Chemokines Combined with Local Tumor Destruction Enhances Tumor Regression and Long-term Immunity, Cancer Research, 63:5505-5512, 2003.
Dairaghi et, al., HHV8-Encoded vMIP-I Selectively Engages Chemokine Receptor CCR8, The Journal of Biological Chemistry, 274:21569-21574, 1999.
Damon et al., Broad Spectrum Chemokine Antagonistic Activity of a Human Poxvirus Chemokine Homolog, Proceedings of the National Academy of Sciences, USA, 95:6403-6407, 1998.

(Continued)

*Primary Examiner* — Nancy J Leith
(74) *Attorney, Agent, or Firm* — Occhiuti & Rohlicek LLP

(57) ABSTRACT

A novel cytokine, U83A, is described, as are variant forms of the cytokine, having a wide range of agonistic and antagonistic activity against chemokine receptors. Uses of the chemokine in treatment of a range of diseases, including cancers and HIV/AIDS, are described.

15 Claims, 16 Drawing Sheets

(56) References Cited

OTHER PUBLICATIONS

DeBruyne et al., Gene Transfer of Virally Encoded Chemokine Antagonists vMIP-II and MC148 Prolongs Cardiac Allograft Survival and Inhibits Donor-Specific Immunity, Gene Therapy, 7:575-582, 2002.
Dejucq et al., Expanded Tropism of Primary Human Immunodeficiency Virus Type 1 R5 Strains to CD4+ T-Cell Lines Determined by the Capacity to Exploit Low Concentrations of CCR5, Journal of Virology, 73:7842-7847, 1999.
Dellacasagrande et al., Liver Metastasis of Cancer Facilitated by Chemokine Receptor CCR6, Scandianavian Journal of Immunology, 57:534-544, 2003.
DiLuca et al., Distribution of HHV-6 Variants in Human Tissues, Infectious Agents and Disease, 5:203-214, 1996 (Abstract only).
Dominguez, Human Herpesvirus 6B Genome Sequence: Coding Content and Comparison with Human Herpesvirus 6A, Journal of Virology, 73:8040-8052, 1999.
Eltayeb et al., Effector Stage CC Chemokine Receptor-1 Selective Antagonism Reduces Multiple Sclerosis-Like Rat Disease, Journal of Neuroimmunology, 142:75-85, 2003.
Emery et al., Interactions Between β-Herpesviruses and Human Immunodeficiency Virus In Vivo: Evidence for Increased Human Immunodeficiency Viral Load in the Presence of Human Herpesvirus 6, Journal of Medical Virology, 57:278-282, 1999.
Endres et al., The Kaposi's Sarcoma-Related Herpesvirus (KSHV)-Encoded Chemokine vMIP-I is a Specific Agonist for the CC Chemokine Receptor (CCR)8, Journal of Experimental Medicine, 189:1993-1998, 1999.
Fairfax et al., Human Herpesvirus 6 DNA in Blood Cells of Human Immunodeficiency Virus-Infected Men: Correlation of High Levels With High CD4 Cell Counts, Journal of Infectious Disease, 169:1342-1345, 1994 (Abstract only).
Ferenczi et al., Increased CCR4 Expression in Cutaneous T Cell Lymphoma, The Journal of Investigative Dermatology, 119:1405-1410, 2002.
Fleming et al., The Murine Cytomegalovirus Chemokine Homolog, m131/129, is a Determinant of Viral Pathogenicity, Journal of Virology, 73:6800-6809, 1999.
French et al., Novel, Nonconsensus Cellular Splicing Regulates Expression of a Gene Encoding a Chemokine-Like Protein That Shows High Variation and is Specific for Human Herpesvirus 6, Virology, 262:139-151, 1999.
Furumoto et al., Induction of Potent Antitumor Immunity by In Siti Targeting of Intratumoral DCs, The Journal of Clinical Investigation, 113:774-783, 2004.
Gazdar et al., Mitogen Requirements for the In Vitro Propagation of Cutaneous T-Cell Lymphomas, Blood, 55:409-417, 1980.
Gerna et al., Dendritic-Cell Infection by Human Cytomegalovirus is Restricted to Strains Carrying Functional UL131-128 Genes and Mediates Efficient Viral Antigen Presentation to CD8+ T Cells, Journal of General Virology,86:275-284, 2005.
Gladue et al., CP-481,715, a Potent and Selective CCR1 Antagonist with Potential Therapeutic Implications for Inflammatory Diseases, 278:40473-40480, 2003.
Gompels et al., The DNA Sequence of Human Herpesvirus-6: Structure, Coding Content, and Genome Evolution, Virology, 209:29-51, 1995.
Hahn et al., Human Cytomegalovirus UL131-128 Genes Are Indispensable for Virus Growth in Endothelial Cells and Virus Transfer to Leukocytes, Journal of Virology, 78:10023-10033, 2004.
Halks-Miller et al., CCR1 is an Early and Specific market of Alzheimer's Disease, Annals of Neurology, 54:638-646, 2003 (Abstract only).
Haringman et al., Chemokine Blockade and Chronic Inflammatory Disease: Proof of Concept in Patients with Rheumatoid Arthritis, Annals of the Rheumatic Diseases, 62:715-721, 2003.
Hromas et al., The Exodus Subfamily of CC Chemokines Inhibits the Proliferation of Chronic Myelogenous Leukemia Progenitors, Blood, 95:1506-1508, 2000.

Isegawa et al., Comparison of the Complete DNA Sequences of Human Herpesvirus 6 Variants A and B, Journal of Virology, 73:8053-8063, 1999.
Isomura et al., Suppressive Effects of Human Herpesvirus 6 on In Vitro Colony Formation of Hematopoietic Progenitor Cells, Journal of Medical Virology, 52:406-412, 1997.
Kasolo et al., Infection with AIDS-Related Herpesviruses in Human Immunodeficiency Virus-Negative Infants and Endemic Childhood Kaposi's Sarcoma in Africa, Journal of General Virology, 78:847-856, 1997.
Kim et al., Detection of Human Herpesvirus 6 Variant A in Peripheral Blood Mononuclear Cells from Multiple Sclerosis Patients, European Neurology, 43:170-173, 2000 (Abstract only).
Kim et al., CCR4-Bearing T Cells Participate in Autoimmune Diabetes, The Journal of Clinical Investigation, 110:1675-1686, 2000.
Kledal et al., A Broad-Spectrum Chemokine Antagonist Encoded by Kaposi's Sarcoma-Associated Herpesvirus, Science, 277:1656-1659, 1997.
Klein et al., Properties of the K562 Cell Line, Derived from a Patient with Chronic Myeloid Leukemia, Intenational Journal of Cancer, 18:421-431, 1976 (Abstract only).
Knox et al., In Vitro Suppression of Bone Marrow Progenitor Cell Differentiation by Human Herpesvirus 6 Infection, Journal of Infectious Diseases, 165:925-929, 1992 (Abstract only).
Knox and Carrigan, Disseminated Active HHV-6 Infections in Patients with AIDS, The Lancet, 343:577-578, 1994 (Abstract only).
Kohler et al., A Role for Macrophage Inflammatory Protein-3(alpha)/CC Chemokine Ligand 20 in Immune Priming during T Cell-Mediated Inflammation of the Central Nervous System, Journal of Immunology, 170:6298-6306, 2003.
Lee et al., CCR8 on Human Thymocytes Functions as a Human Immunodeficiency Virus Type 1 Coreceptor, Journal of Virology, 74:6946-6952, 2000.
Lezcano-Meza et al., The Monocyte-Derived Chemokine is Released in the Bronchoalveolar Lavage Fluid of Steady-State Asthmatics, Allergy, 58:1125-1130, 2003.
Li et al., Complete Regression of Experimental Solid Tumors by Combination LEC/chTNT-3 Immunotherapy and CD25+ T-Cell Depletion, Cancer Research, 63:8384-8392, 2003.
Liang et al., Identification and Characterization of a Potent, Selective, and Orally Active Antagonist of the CC Chemokine Receptor-1, The Journal of Biological Chemistry, 275:19000-19008, 2000.
Lin et al., Herpesviruses in Brain and Alzheimer's Disease, Journal of Pathology, 197:395-402, 2002 (Abstract only).
Lüttichau et al., A Highly Selective CCR2 Chemokine Agonist Encoded by Human Herpesvirus 6, The Journal of Biological Chemistry, 278:10928-10933, 2003.
Lüttichau et al., MC148 Encoded by Human Molluscum Contagiosum Poxvirus is an Antagonist for Human But Not Murine CCR8, Journal of Leukocyte Biology, 70:277-282, 2001.
Lüttichau et al., A Highly Selective CC Chemokine Receptor (CCR)8 Antagonist Enclode by the Poxvirus *Molluscum contagiosum,* Journal of Experimental Medicine, 191:171-179, 2000.
Lüttichau et al., The Herpesvirus 8-Encoded Chemokine vMIP-II, but not the Poxvirus-Encoded Chemokine MC148, Inhibits the CCR10 Receptor, European Journal of Immunology, 31:1217-1220, 2001.
Milne et al., RANTES Binding and Down-Regulation by a Novel Human Herpesvirus-6 β Chemokine Receptor, The Journal of Immunology, 164:2396-2404, 2000.
Nicholas, Determination and Analysis of the Complete Nucleotide Sequence of Human Herpesvirus 7, Journal of Virology, 70:5975-5989, 1996.
Nitsche et al., Inhibition of Cord Blood Cell Expansion by Human Herpesvirus 6 In Vitro, Stem Cells and Development, 13:197-203, 2004 (Abstract only).
Pal et al., Inhibition of HIV-1 Infection by the β-Chemokine MDC, Science, 278:695-698, 1997.

(56) References Cited

OTHER PUBLICATIONS

Panina-Bordignon et al., The C-C Chemokine Receptors CCR4 and CCR8 Identify Airway T Cells of Allergen-Challenged Atopic Asthmatics, The Journal of Clinical Investigation, 107:1357-1364, 2001.
Penfold et al., Cytomegalovirus Encodes a Potent α Chemokine, Proceedings of National Academy of Sciences of the USA, 96:9839-9844, 1999.
Penfold et al., A Macrophage Inflammatory Protein Homolog Encoded by Guinea Pig Cytomegalovirus Signals Via CC Chemokine Receptor 1, Virology, 316:202-212, 2003.
Robinson et al., A Chemokine Receptor Antagonist Inhibits Experimental Breast Tumor Growth, Cancer Research, 63:8360-8365, 2003.
Rotola et al., Human Herpesvirus 6 Infects the Central Nervous System of Multiple Sclerosis Patients in the Early Stages of the Disease, Multiple Sclerosis, 10:348-354, 2004 (Abstract only).
Rottman et al., Leukocyte Recruitment During Onset of Experimental Allergic Encephalomyelitis is CCR1 Dependent, European Journal of Immunology, 30:2372-2377, 2000.
Ruckes et al., Autocrine Antiapoptotic Stimulation of Cultured Adult T-Cell Leukemia Cells by Overexpression of Chemokine I-309, Blood, 98:1150-1159, 2001.
Saederup et al., Murine Cytomegalovirus CC Chemokine Homolog MCK-2 (m131-129) is a Determinant of Dissemination That Increases Inflammation at Initial Sites of Infection, Journal of Virology, 75:9966-9976, 2001.
Saederup et al., Cytomeglovirus-Encoded β Chemokine Promotes Monocyte-Associates Viremia in the Host, Proceedings of National Academy of Sciences of the USA, 96:10881-10886, 1999.
Smith et al., Single-Step Purification of Polypeptides Expressed in *Escherichia coli* as Fusions with Glutathione S-Transferase, Gene, 67:31-40, 1988 (Abstract only).
Soldan et al., Increased Lymphoproliferative Response to Human Herpesvirus Type 6A Variant in Multiple Sclerosis Patients, Annals of Neurology, 47:306-313, 2000 (Abstract only).
Sozzani et al., The Viral Chemokine Macrophage Inflammatory Protein-II is a Selective Th2 Chemoattractant, Blood, 92:4036-4039, 1998.
Spenlehauer, A Luciferase-Reporter Gene-Expressing T-Cell Line Facilitates Neutralization and Drug-Sensitivity Assays That Use Either R5 or X4 Strains of Human Immunodeficiency Virus Type 1, Virology, 280:292-300, 2001.
Spinetti et al., The Chemokine Receptor CCR8 Mediates Rescue from Dexamethasone-Induced Apoptosis Via an ERK-Dependent Pathway, Journal of Leukocyte Biology, 73:201-207, 2003.
Stine et al., KSHV-Encoded CC Chemokine vMIP-III is a CCR4 agonist, Stimulates Angiogenesis, and Selectively Chemoattracts TH2 Cells, Blood, 95:1151-1157, 2000.
Struyf et al., Cutting Edge: Enhanced Anti-HIV-1 Activity and Altered Chemotactic Potency of NH2-Terminally Processed Macrophage-Derived Chemokine (MDC) Imply an Additional MDC Receptor, The Journal of Immunology, 161:2672-2675, 1998.
Sunnemark, et al., Differential Expression of the Chemokine Receptors CX3CR1 and CCR1 by Microglia and Macrophages in Myelin-Oligodendrocyte-Glycoprotein-Induced Experimental Autoimmune Encephalomyelitis, Brain Pathology, 13:617-629, 2003 (Abstract only).
Trebst et al., Chemokine Receptors on Infiltrating Leucocytes in Inflammatory Pathologies of the Central Nervous System (CNS), Neuropathology and Applied Neurobiology, 29:584-595, 2003 (Abstract only).
Tsuchiya et al., Establishment and Characterization of a Human Acute Monocytic Leukemia Cell Line (THP-1), International Journal of Cancer, 26:171-176, 1980.
Utaipat et al., Coreceptor Utilization of HIV Type 1 Subtype E Viral Isolates from Thai Men with HIV Type 1-Infected and Uninfected Wives, AIDS Research and Human Retroviruses, 18:1-11, 2002.
Yang et al., Many Chemokines Including CCL20/MIP-3α Display Antimicrobial Activity, Journal of Leukocyte Biology, 74:448-455, 2003.
Yoshie et al., Frequent Expression of CCR4 in Adult T-Cell Leukemia and Human T-Cell Leukemia Virus Type 1-Transformed T Cells, Blood, 99:1505-1511, 2002.
Zhang et al., Mobilization of Dendritic Cell Precursors Into the Circulation by Administration of MIP-1α in Mice, Journal of the National Cancer Institute, 96:201-209, 2004.
Zibert, A, et al., CCL3/MIP-1alpha is a potent immunostimulator When Coexpressed with Interleukin-2 or Granulocyte-Macrophage Colony-Stimulating Factor in a Leukemia/Lymphoma Vaccine, Human Gene Therapy, 15:21-34, 2004 (Abstract only).
Zou et al., Human Herpesvirus 6 Open Reading Frame U83 Encodes a Functional Chemokine, Journal of Virology, 73:5926-5933, 1999.

\* cited by examiner

FIG. 15 SEQ ID NO 1: U83A nucleotide sequence with polymorphism underlined leading to frameshift and utilisation of upstream ATG start codon.

```
atgtccattcggcttttattggttttttttatacggcatatattggtatggctatcggatttatgta
gttccccgatgcggagctgttttccgaaaatcacgtatgtcgtcttctgttctgttaggatgttgtt
gtgttgcatgaaaacttttgatgcaatcatgatcatgtgcttctgcttaccgtctgatttggagcaggctcgatgtgata
atgattaaaaagctaaaaagttgtttctgcttaccgtctgattagattgtcgaaattagacaaagaatca
tggcagatgcatcgccgacaagtcttgaattagacaaagaatca
```

FIG. 16 SEQ ID NO 2: U83A nucleotide sequence without secretory signal portion

```
tttatatgtagttccccgatgcggagctgttttccgaaaatcacgtatgtcgtcttct
gtcttgttaggatgttgtttgcatgttgcatgaaaactttttgatgcaatcatgatcatgtgcctgtacctgccgaaaaca
gagccttttagaaaactttttgatgcaatcatgatcatgtgcctaaaaagttgttctgct
gcttacccgtctgatttggagcaggctcgatgtgtgatatggcagatgcatcgccgaca
agtcttgaattagacaaagaatca
```

FIG. 17 SEQ ID NO 3: U83A-Npep nucleotide sequence, spliced cDNA coding sequence

```
atgtccattcggcttttattggttttttttatacggcatatattggtatggctatcgga
tttatatgtagttccccgatgcggagctgtttttccgaaaatcacgtatgtcgtcttct
gtcttgttaggatgttgtttgcatgttgcatgattggtccgctgccgtacccgtctga
```

FIG. 18

SEQ ID NO 4: U83A-Npep nucleotide sequence without secretory signal portion from spliced cDNA coding sequence

```
tttatatgtagttccccgatgcggagctgttttccgaaaatcacgtatgtcgtcttct    60
gtcttgttaggatgtttgttgttgcatggattgtccgtccgctgccgctaccgtctctga 113
```

FIG. 19

SEQ ID NO 5: A. U83A amino acid sequence

```
MSIRLFIGFF YTAYIGMAIG FICSSPDAEL FSEKSRMSSS VLLGCLLCCM DWSAAVPGKT    60
EPFRKLFDAI MIKKLKSCSA AYPSDLEQGS MCDMADASPT SLELGLSKLD KES         113
```

FIG. 20

SEQ ID NO 6: U83A amino acid sequence without secretory signal portion

```
FICSSPDAEL FSEKSRMSSS VLLGCLLCCM DWSAAVPGKT EPFRKLFDAI MIKKLKSCSA    60
AYPSDLEQGS MCDMADASPT SLELGLSKLD KES                                 93
```

FIG. 21

SEQ ID NO 7: U83A-Npep amino acid sequence

MSIRLFIGFF YTAYIGMAIG FICSSPDAEL FSEKSRMSSS VLLGCLLCCM DWSAAVPV

FIG. 22

SEQ ID NO 8: U83A-Npep amino acid sequence without secretory signal portion

FICSSPDAEL FSEKSRMSSS VLLGCLLCCM DWSAAVPV

CYTOKINE

CROSS-REFERENCE TO RELATED APPLICATIONS

This application is a continuation of U.S. application Ser. No. 11/915,524, filed Sep. 12, 2008 (now U.S. Pat. No. 8,940,686), which is a U.S. national phase application filed under 35 U.S.C. §371 of International Application No. PCT/GB2006/050121, filed May 25, 2006, which claims the benefit of the priority date of Great Britain Application No. 0510559.8, filed May 25, 2005. The contents of the aforementioned applications are hereby incorporated by reference in their entirety.

FIELD OF THE INVENTION

The present invention relates to a cytokine. Aspects of the invention relate to forms of the cytokine having agonistic effects on a range of cytokine receptors, while further aspects of the invention relate to forms of the cytokine having antagonistic effects on a range of cytokine receptors. Other aspects of the invention relate to treatment of various disorders characterised by aberrant cytokine activity; and to use of the cytokine as an adjuvant or diagnostic; or as screens for inhibitors of function or for processing of the cytokine gene.

BACKGROUND TO THE INVENTION

Human herpesvirus 6, HHV-6, exists in at least two strain groups: variant A and variant B, HHV-6A and HHV-6B. They are closely related, averaging 5% in herpesvirus conserved genes with greater divergence at the ends of the genomes and selected sites between conserved gene blocks (1-3). These variants are related to a smaller genome of human herpesvirus 7 (HHV-7) forming the Roseoloviruses and together with the more distant human cytomegalovirus form the betaherpesvirus subgroup of the herpesvirus family, maintaining a conserved gene order and similarity in sites of latency including monocytic/macrophage cell types. HHV-6A and HHV-6B have differing geographic prevalence with HHV-6B dominant in USA, Europe and Japan, while HHV-6A appears only a minor variant except in African countries where it appears equally prevalent to HHV-6B (4, 5). However exhaustive surveys have not been conducted using serological specific reagents given the close relation between these viruses. There are hotspots for variation between representatives of these virus genomes and these may contribute to some cellular tropism and pathological differences which have been anecdotally reported. For example, only HHV-6A has been detected in skin biopsies and HHV-6A has been increasingly implicated in cases of multiple sclerosis where careful genotyping and identification of active infections have been carried out (5-10). These studies either implicate immune abnormalities in clearance of the virus or possible complications of rare primary adult infection with this variant, since in countries where this has been studied HHV-6B is the predominant variant identified.

Both HHV-6A and HHV-6B have cellular tropisms for CD4+ T-lymphocytes, and both are neurotropic, although there may be differences in the exact site of latency given the more disperse detection of HHV-6A where studies have been undertaken. Interestingly, the chemokine encoded by HHV-6 is highly divergent between these strain variant groups and thus would be a major candidate for determining pathogenic differences.

Chemokines are main mediators of an inflammatory response and can control chemotaxis of leukocyte populations to an infectious centre. In HCMV, for example, the UL146 chemokine is specific for alpha chemokines and can control dissemination of the virus in specifically chemoattracted neutrophils. There is another locus encoding an HCMV chemokine, UL126, and this also appears to affect cellular tropism, in that passage in fibroblasts results in deletion or alteration to this gene (11-13). This gene has similarities to betachemokines which can chemoattract monocytes and a similar function in murine CMV, vMCK, has been shown essential for virus dissemination (14-16). In HHV-6, there is a single chemokine gene, which is deleted in HHV-7, the highly variable U83. In HHV-6B this molecule (referred to as U83B) has been characterised as an efficient selective CCR2 agonist although with low potency (17). Earlier studies have shown chemotactic activity for monocytic THP-1 cells which express this receptor (18) and are consistent with the role of monocytic cells as sites for latent infection.

The published sequence of the U83 gene from HHV-6A, U83A, includes a signal sequence predicted not to permit secretion of the gene product. As a consequence, the U83A gene product is believed unlikely to have any chemokine-like properties.

The present inventors have surprisingly identified that the U83A sequence is polymorphic, with a novel sequence described herein having a functional secretory signal sequence. The present inventors have also identified that the secreted peptide has agonistic and antagonistic properties against a remarkably wide range of chemokine receptors. The U83A product is also produced in a short splice variant, U83A-Npep, which displays antagonistic properties against a range of chemokine receptors.

SUMMARY OF THE INVENTION

According to a first aspect of the present invention, there is provided an isolated polynucleotide comprising the sequence of SEQ ID NO 1, or SEQ ID NO 2, or SEQ ID NO 3, or SEQ ID NO 4. The novel U83A sequence, including the polymorphism and the full secretory signal sequence is given in SEQ ID NO 1; SEQ ID NO 2 is the same sequence without the secretory signal sequence. The nucleotide sequence corresponding to the short splice variant, U83A-Npep, is given in SEQ ID NO 3 with the secretory signal sequence, and in SEQ ID NO 4 without the secretory signal sequence. The invention also includes polynucleotides complementary to such sequences, and polynucleotides which hybridise under stringent conditions to these polynucleotides. 'Hybridise under stringent conditions' means that there is hybridisation between two polynucleotide sequences at 65° C. or calculated sequence-specific melting points after washing with 0.2×SSC. Details of detection of hybridisation of nucleotide sequences will be known to the skilled person.

The invention also provides an isolated polynucleotide encoding the amino acid sequence of SEQ ID NO 5, or SEQ ID NO 6, or SEQ ID NO 7, or SEQ ID NO 8. The amino acid sequences of SEQ ID NOS 5 to 8 correspond to the nucleotide sequences of SEQ ID NOS 1 to 4 respectively. The invention also includes polynucleotides complementary to such polynucleotides, and those which hybridise under stringent conditions thereto.

The invention further provides vectors comprising the above polynucleotide sequences, and host cells comprising such vectors. Vectors may include plasmids, cosmids, artificial chromosomes, and the like. Preferably the vector is an expression vector. The host cell may be prokaryotic or eukaryotic, and may include bacterial cells, fungal cells such as yeast, plant cells, insect cells, or mammalian cells. Also provided is a host cell comprising an exogenous polynucleotide according to the above aspects of the invention. Preferably the host cell expresses said polynucleotide.

According to a further aspect of the invention, there is provided a polypeptide comprising the amino acid sequence of SEQ ID NO 5, or SEQ ID NO 6, or SEQ ID NO 7, or SEQ ID NO 8. The invention further extends to variants and derivatives of such polypeptides; that is, modified polypeptides having the same or similar functional effects. Variants may include, for example, conservative amino acid substitutions, deletions, or additions as described below. The invention further extends to polynucleotide sequences encoding such polypeptides.

Preferably the polypeptides of the present invention are active as chemokines; alternatively, or in addition, they may act as agonists and/or antagonists to chemokine receptors.

The polypeptides of the present invention may comprise additional amino acids; for example, N-terminal additions of GS, or of GSRDDDDK (SEQ ID NO 15), or of GSRIEGR (SEQ ID NO 16). Other additional sequences may also or instead be used. The polypeptides of the present invention may include additional sequences useful in purification of the polypeptide. For example, cleavage recognition sequences such as thrombin, enterokinase, or factor Xa recognition sequences.

A further aspect of the present invention provides a method of purifying such polypeptides, the method comprising expressing a vector comprising the nucleotide sequence of SEQ ID NO 1, or SEQ ID NO 2, or SEQ ID NO 3, or SEQ ID NO 4 in a host cell, the vector additionally comprising a nucleotide sequence encoding a binding tag; allowing the expressed polypeptide to bind to the target of said binding tag; and causing said bound polypeptide to be released from said target. The host cell may be eukaryotic, for example, a mammal, other vertebrate or invertebrate, insect, fungal, or plant cell; or may be prokaryotic, for example, bacterial; and may use vectors of bacterial, yeast, other eukaryotic, other non-eukaryotic, or virus sequence origin.

Preferably the binding tag binds glutathione; the tag may be glutathione S-transferase (GST). The binding tag target is preferably immobilised on a solid support; this allows the bound polypeptide to be easily isolated from unbound product. Other suitable binding tags immobilised on similar solid supports could be used.

The vector may further encode a cleavage recognition site; preferably this site is within or adjacent the binding tag. The recognition site may be for thrombin, enterokinase, or factor Xa, among others. The method may then comprise the step of cleaving the polypeptide at the recognition site.

Polypeptides of the present invention may be useful as cytokines, or as agonists or antagonists of cytokine receptors. Thus, according to a further aspect of the present invention there is provided a method of activating a cytokine receptor, the method comprising administering a polypeptide comprising the sequence of SEQ ID NO 5 or SEQ ID NO 6, or a variant or derivative thereof, to a target cell, or to a patient. Polynucleotide sequences of the invention may be administered in such a method. The cytokine receptor to be activated is preferably one or more of CCR1, CCR4, CCR5, CCR6, and CCR8. In one embodiment, the cytokine receptor to be activated is preferably one or more of CCR1, CCR4, CCR6, and CCR8.

Also provided is a method of treating a disease characterised by reduced levels of activation of one or more of CCR1, CCR4, CCR5, CCR6, and CCR8, the method comprising administering a polypeptide comprising the sequence of SEQ ID NO 5 or SEQ ID NO 6, or a variant or derivative thereof, or a polynucleotide encoding such a polypeptide to a target cell, or to a patient. In one embodiment, the method comprises of treating a disease characterised by reduced levels of activation of one or more of CCR1, CCR4, CCR6, and CCR8. The invention also provides the use of a polypeptide comprising the sequence of SEQ ID NO 5 or SEQ ID NO 6 or a variant or derivative thereof, or a polynucleotide encoding such a polypeptide in the preparation of a medicament for the treatment of a disease characterised by reduced levels of activation of one or more of CCR1, CCR4, CCR5, CCR6, and CCR8. In one embodiment, the use is of a polypeptide comprising the sequence of SEQ ID NO 5 or SEQ ID NO 6 or a variant or derivative thereof, or a polynucleotide encoding such a polypeptide in the preparation of a medicament for the treatment of a disease characterised by reduced levels of activation of one or more of CCR1, CCR4, CCR5, CCR6, and CCR8.

The present invention also provides a method of preventing activation of a cytokine receptor, the method comprising administering a polypeptide comprising the sequence of SEQ ID NO 5 or SEQ ID NO 6 or a variant or derivative thereof, or a polynucleotide encoding such a polypeptide to a target cell, or to a patient. The cytokine receptor to be prevented from activation is preferably one or more of CCR1, CCR4, CCR5, CCR6, and CCR8. In one embodiment, the cytokine receptor to be prevented from activation is preferably one or more of CCR1, CCR4, CCR6, and CCR8. Also provided is a method of treating a disease characterised by elevated levels of activation of one or more of CCR1, CCR4, CCR5, CCR6, and CCR8, the method comprising administering a polypeptide comprising the sequence of SEQ ID NO 5 or SEQ ID NO 6 or a variant or derivative thereof, or a polynucleotide encoding such a polypeptide to a target cell, or to a patient. In one embodiment, the method of treating a disease characterised by elevated levels of activation of one or more of CCR1, CCR4, CCR6, and CCR8. The invention also provides the use of a polypeptide comprising the sequence of SEQ ID NO 5 or SEQ ID NO 6 or a variant or derivative thereof, or a polynucleotide encoding such a polypeptide in the preparation of a medicament for the treatment of a disease characterised by elevated levels of activation of one or more of CCR1, CCR4, CCR5, CCR6, and CCR8. In one embodiment, the use is of a polypeptide comprising the sequence of SEQ ID NO 5 or SEQ ID NO 6 or a variant or derivative thereof, or a polynucleotide encoding such a polypeptide in the preparation of a medicament for the treatment of a disease characterised by elevated levels of activation of one or more of CCR1, CCR4, CCR6, and CCR8.

Also provided is a method of preventing activation of a cytokine receptor, the method comprising administering a polypeptide comprising the sequence of SEQ ID NO 7 or SEQ ID NO 8 or a variant or derivative thereof, or a polynucleotide encoding such a polypeptide to a target cell, or to a patient. The cytokine receptor to be prevented from activation is preferably one or more of CCR1, CCR4, CCR5, CCR6 or CCR8. In one embodiment, the cytokine receptor to be prevented from activation is preferably one or more of CCR1, or CCR5. Also provided is a method of treating a disease characterised by elevated levels of activation of one or more of CCR1, CCR4, CCR5, CCR6 or CCR8, the method comprising administering a polypeptide comprising the sequence of SEQ ID NO 7 or SEQ ID NO 8 or a variant or derivative thereof, or a polynucleotide encoding such a polypeptide to a target cell, or to a patient. In one embodiment, the method relates to treating a disease characterised by elevated levels of activation of one or more of CCR1 or CCR5. The invention also provides the use of a polypeptide comprising the sequence of SEQ ID NO 7 or SEQ ID NO 8 or a variant or derivative thereof, or a polynucleotide encoding such a polypeptide in the preparation of a medicament for the treatment of a disease characterised by elevated levels of activation of one or more of CCR1, CCR4, CCR5, CCR6 or CCR8. In one embodiment, the method relates to the use wherein the disease is characterised by elevated levels of activation of one or more of CCR1 or CCR5.

The invention also provides the use of a polypeptide comprising the amino acid sequence of SEQ ID NO 5, or SED ID NO 6, or SEQ ID NO 7, or SEQ ID NO 8, or a variant or derivative thereof, or a polynucleotide encoding such a polypeptide as a medicament. Also provided is a pharmaceutical composition comprising a polypeptide comprising the amino acid sequence of SEQ ID NO 5, or SED ID NO 6, or SEQ ID NO 7, or SEQ ID NO 8 or a variant or derivative thereof, or a polynucleotide encoding such a polypeptide.

Administration of pharmaceutical compositions of the invention may be accomplished orally or parenterally. Methods of parenteral delivery include topical, intra-arterial, intramuscular, subcutaneous, intramedullary, intrathecal, intraventricular, intravenous, intraperitoneal, mucosal or intranasal administration. In addition to the active ingredients, such compositions may comprise suitable pharmaceutically acceptable carriers comprising excipients and other components which facilitate processing of the active compounds into preparations suitable for pharmaceutical administration.

Pharmaceutical compositions for oral administration can be formulated using pharmaceutically acceptable carriers known in the art in dosages suitable for oral administration. Such carriers enable the compositions to be formulated as tablets, pills, dragees, capsules, liquids, gels, syrups, slurries, suspensions, and the like suitable for ingestion by the subject.

Pharmaceutical preparations for oral use can be obtained through combination of active compounds with a solid excipient, optionally grinding a resulting mixture, and processing the mixture of granules, after adding suitable additional compounds if desired to obtain tablets or dragee cores. Suitable excipients include carbohydrate or protein fillers such as sugars, including lactose, sucrose, mannitol, sorbitol; starch from corn, wheat, rice, potato, or other plants; cellulose such as methylcellulose, hydroxypropylmethylcellulose, or sodium carboxymethylcellulose; and gums including arabic and tragacanth; as well as proteins such as gelatin and collagen. If desired, disintegrating or solubilising agents may be added, such as cross linked polyvinyl pyrrolidone, agar, alginic acid, or a salt thereof.

Dragee cores can be provided with suitable coatings such as concentrated sugar solutions, which may also contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for product identification or to characterise the quantity of active compound.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally stabilisers. In soft capsules, the active compounds can be dissolved or suspended in suitable liquids, such as fatty oils, liquid paraffin, or liquid polyethylene glycol with or without stabilisers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous suspension injections can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension can also contain suitable stabilisers or agents which increase the solubility of the compounds to allow for the preparation of highly concentrated solutions. Pharmaceutical compositions may also include adjuvants to enhance or modulate antigenicity.

For topical or nasal administration, penetrants appropriate to the particular bather to be permeated may be used in the formulation.

The pharmaceutical compositions of the present invention can be manufactured substantially in accordance with standard manufacturing procedures known in the art.

The present invention further provides the use of a polypeptide comprising the amino acid sequence of SEQ ID NO 5, or SEQ ID NO 6, or a variant or derivative thereof, or a polynucleotide encoding such a polypeptide as an agonist to a cytokine receptor. Also provided is the use of a polypeptide comprising the amino acid sequence of SEQ ID NO 5, or SEQ ID NO 6, or SEQ ID NO 7, or SEQ ID NO 8, or a variant or derivative thereof, or a polynucleotide encoding such a polypeptide as an antagonist to a cytokine receptor.

Still further aspects of the present invention provide a vaccine composition comprising a polypeptide comprising the amino acid sequence of SEQ ID NO 5, or SEQ ID NO 6, or SEQ ID NO 7, or SEQ ID NO 8 or a variant or derivative thereof, or a polynucleotide encoding such a polypeptide. The use of a polypeptide comprising the amino acid sequence of SEQ ID NO 5, or SEQ ID NO 6, or SEQ ID NO 7, or SEQ ID NO 8 or a variant or derivative thereof, or a polynucleotide encoding such a polypeptide in the preparation of a vaccine is also provided, as is the use of a polypeptide comprising the amino acid sequence of SEQ ID NO 5, or SEQ ID NO 6, or SEQ ID NO 7, or SEQ ID NO 8 or a variant or derivative thereof, or a polynucleotide encoding such a polypeptide as an adjuvant.

Vaccines according to the invention may be formulated for mucosal skin administration.

Nucleotides of the present invention may also be used as DNA vaccines or immunotherapeutics or to enhance antigenicity of co-delivered polypeptides or DNA encoding polypeptides.

According to a further aspect of the present invention, there is provided a method of treatment of a disease selected from cancer; HIV infection, HIV/AIDS; Alzheimer's; and diseases having an autoimmune inflammatory component, including multiple sclerosis, rheumatoid arthritis, asthma, diabetes, lupus, transplant rejection, atherosclerosis, and inflammatory bowel disease; the method comprising administering a polypeptide comprising the amino acid sequence of SEQ ID NO 5, or SEQ ID NO 6, or SEQ ID NO 7, or SEQ ID NO 8 to a patient. In one embodiment, there is provided a method of treatment of HIV infection and/or HIV/AIDS, the method comprising administering a polypeptide comprising the amino acid sequence of SEQ ID NO 5, or SEQ ID NO 6, or SEQ ID NO 7, or SEQ ID NO 8, or a polynucleotide encoding such a polypeptide, to a patient.

The invention also provides the use of a polypeptide comprising the amino acid sequence of SEQ ID NO 5, or SEQ ID NO 6, or SEQ ID NO 7, or SEQ ID NO 8 in the preparation of a medicament for the treatment of a disease selected from cancer; HIV infection, HIV/AIDS; Alzheimer's; and diseases having an autoimmune inflammatory component, including multiple sclerosis, rheumatoid arthritis, asthma, diabetes, lupus, transplant rejection, atherosclerosis, and inflammatory bowel disease. In one embodiment, the invention provides the use of a polypeptide comprising the amino acid sequence of SEQ ID NO 5, or SEQ ID NO 6, or SEQ ID NO 7, or SEQ ID NO 8 in the preparation of a medicament for the treatment of HIV infection and/or HIV/AIDS. Also provided are methods of treatment with, or uses of, derivatives of SEQ ID NO 5, or SEQ ID NO 6, or SEQ ID NO 7, or SEQ ID NO 8 or polynucleotide sequences of the invention.

According to a further aspect of the present invention, the amino acid sequence of SEQ ID NO 5, or SEQ ID NO 6, or SEQ ID NO 7, or SEQ ID NO 8 or a derivative or variant thereof may form part of a combination therapy. In one embodiment, there is provided a method of treatment of HIV infection and/or HIV/AIDS comprising administering the amino acid sequence of SEQ ID NO 5, or SEQ ID NO 6, or SEQ ID NO 7, or SEQ ID NO 8 or a derivative or variant thereof to a patient in combination with another anti-HIV therapeutic agent. By HIV therapeutic agent is meant a drug or vaccine or other agent useful in therapy. The combination may be synergistic. The amino acid sequence of SEQ ID NO 5, or SEQ ID NO 6, or SEQ ID NO 7, or SEQ ID NO 8 or a derivative or variant thereof, or a polynucleotide encoding such an amino acid sequence, may be provided as part of the same medicament or as a separate medicament for administration at the same time or different time as the other anti-HIV therapeutic agent.

The invention also provides the use of a polypeptide comprising the amino acid sequence of SEQ ID NO 5, or SEQ ID NO 6, or SEQ ID NO 7, or SEQ ID NO 8 or a derivative or variant thereof in the preparation of a medicament for the treatment of HIV employing said polypeptide sequence in a synergistic combination with another anti-HIV therapeutic agent.

The other anti-HIV therapeutic agent according to the invention may be a HIV replication inhibitors, HIV vaccines or HIV entry inhibitors such as peptide or nucleotide sequence encoding peptide or small molecule drugs with block infection through CCR5 or other HIV receptors.

The invention still further provides a method of treating bacterial infections, comprising administering a polypeptide comprising the amino acid sequence of SEQ ID NO 5, or SEQ ID NO 6, or SEQ ID NO 7, or SEQ ID NO 8 or a variant or derivative thereof, or a polynucleotide encoding such a polypeptide to a patient. The invention also provides the use of a polypeptide comprising the amino acid sequence of SEQ ID NO 5, or SEQ ID NO 6, or SEQ ID NO 7, or SEQ ID NO 8 or a variant or derivative thereof, or a polynucleotide encoding such a polypeptide in the preparation of an antibacterial composition. An antibacterial composition comprising a polypeptide comprising the amino acid sequence of SEQ ID NO 5, or SEQ ID NO 6, or SEQ ID NO 7, or SEQ ID NO 8 or a variant or derivative thereof, or a polynucleotide encoding such a polypeptide is also provided.

BRIEF DESCRIPTION OF THE DRAWINGS

The present invention will now be described by way of example only and with reference to the accompanying drawings, in which:

FIG. 15 shows the U83A nucleotide sequence identified herein;

FIG. 16 shows the U83A nucleotide sequence without the secretory signal portion;

FIG. 17 shows the U83A-Npep nucleotide sequence;

FIG. 18 shows the U83A-Npep nucleotide sequence without the secretory signal portion;

FIG. 19 shows the U83A amino acid sequence identified herein;

FIG. 20 shows the U83A amino acid sequence without the secretory signal portion;

FIG. 21 shows the U83A-Npep nucleotide sequence; and

FIG. 22 shows the U83A-Npep nucleotide sequence without the secretory signal portion.

DETAILED DESCRIPTION OF THE DRAWINGS

Figure Legends

FIG. 1. Purification of U83A. A, Shown are traces (A280 nm) from three separate purifications using reversed phase high pressure liquid chromatography. B, Silver-stained SDS-PAGE of peak fractions show the separation of native U83A in fractions 49 and 50, from uncleaved U83GST fusion protein and cleaved GST in fractions 56-60.

Figure 2A:
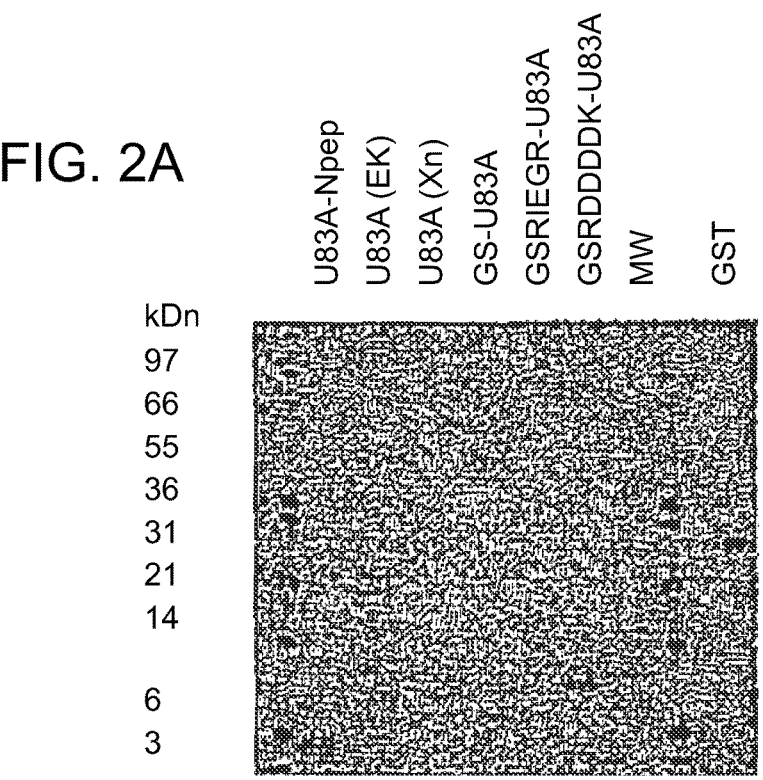
FIGS. 2A-2C show identification of the purified U83A variations by western blot.

FIG. 2. Identification of purified U83A and variants by Western blot. A, Silver stained SDS-PAGE showing HPLC purified U83A-Npep, U83A purified after EK cleavage, U83A(EK) (EK-U83-GST construct), or after Xa cleavage U83A(Xa) (Xa-U83-GST construct), or N-terminal variants of U83A as indicated (GS-U83A, GSRIEGR-U83A, GSRDDDDK-U83A) purified after thrombin digestion of constructs U83A-GST, Xa-U83-GST (factor Xa site N-terminal modified U83A), and EK-U83A-GST (enterokinase site N-terminal modified U83A). MW are molecular weight markers as indicated and GST is the HPLC purified GST moiety. B, Western blot results using anti-U83A intron peptide sera identified native full-length U83A and N-terminal variants. C, Control Western blot results using anti-GST sera confirm specificity and purity, identifying only the GST.

Figure 3A:
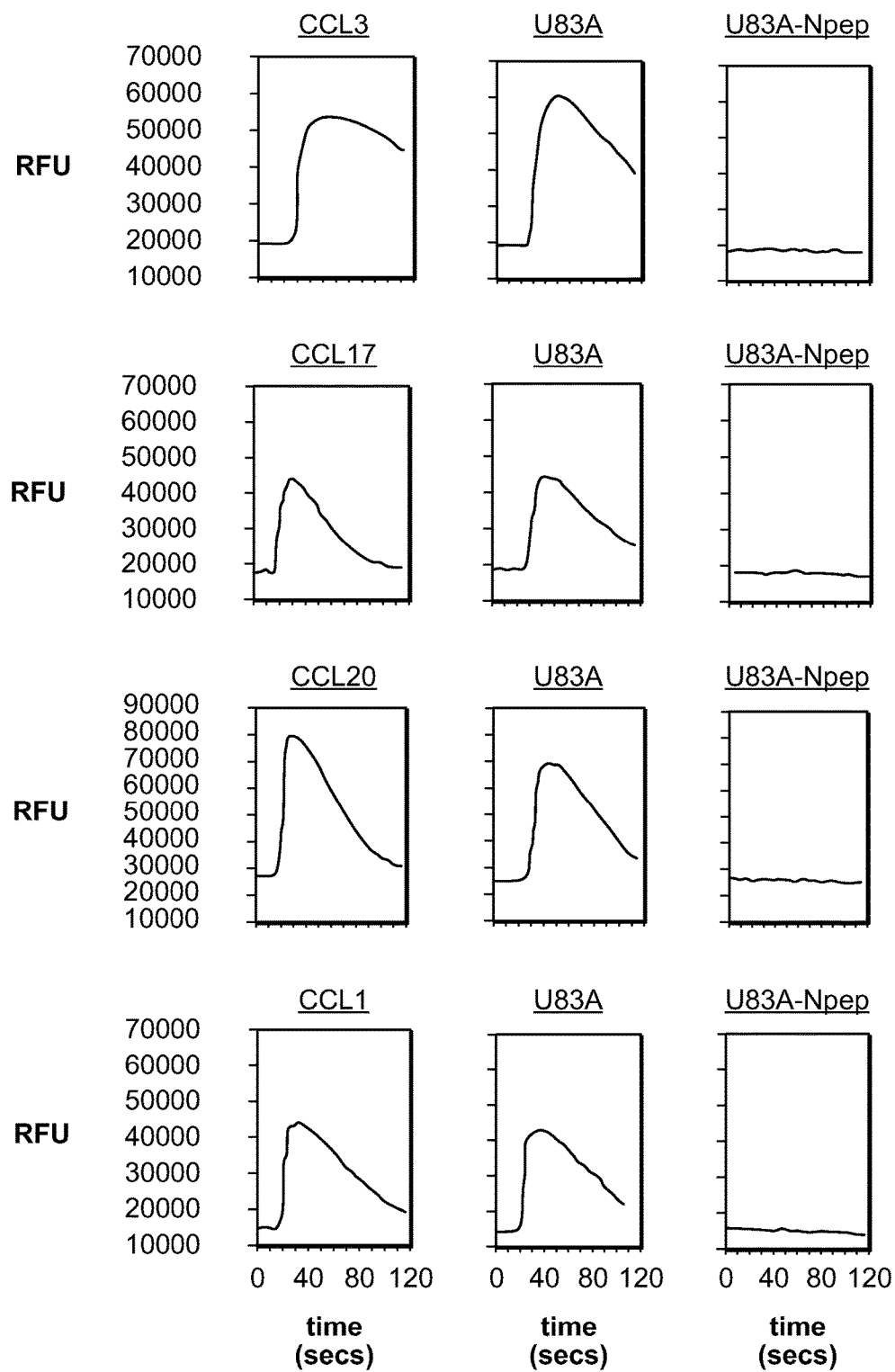
FIGS. 3A-3B show binding responses of CHO cells expressing specific chemokine receptors to U83A.
Figure 3B:
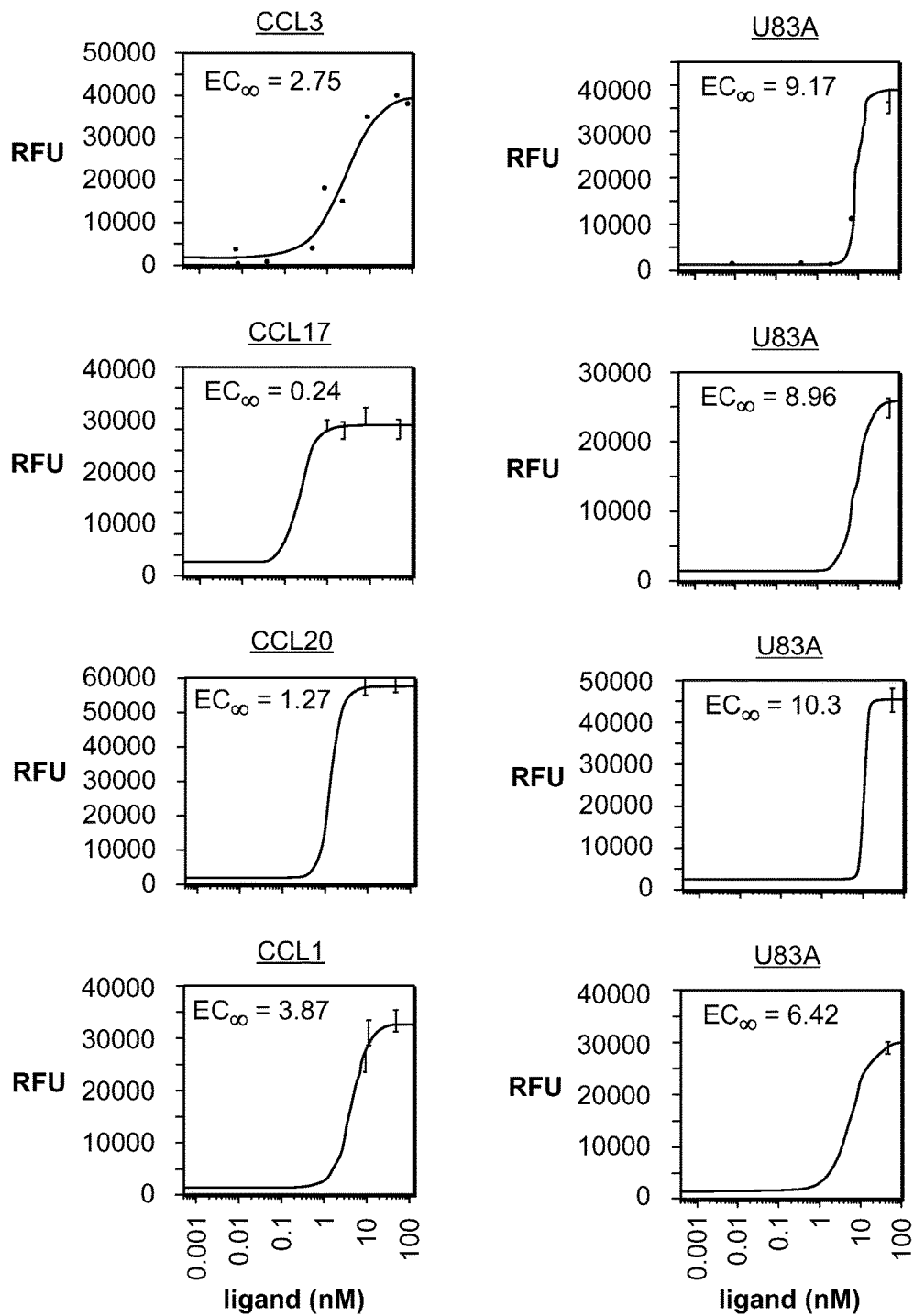

FIG. 3. Induction of intracellular calcium mobilisation using U83A and human endogenous chemokine ligands. A, CHO cell lines stably transfected with CCR1, CCR4, CCR6 and CCR8 and labelled with Fluo-3 are treated after 20 secs with 50 nM U83A, U83A-Npep or endogenous human chemokine ligands CCL3, CCL20, CCL17 and CCL1 respectively. RFU are relative fluorescent unit, indicating relative levels of induction of calcium mobilisation. B, EC50s were calculated as indicated from measuring peak induction levels after stimulation with 100, 50, 10, 7.5, 2.5, 1 nM concentrations of indicated U83A or human chemokines. Negative controls were the vehicle buffer without added chemokine.

Figure 4:
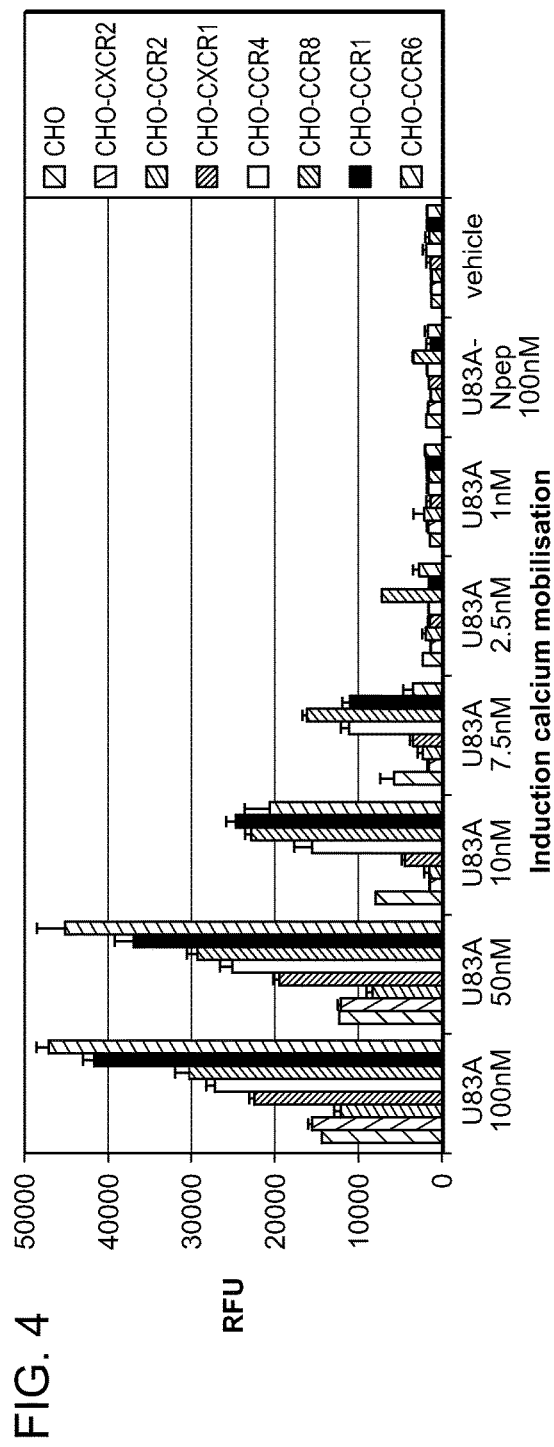
FIG. 4 shows dose responses of U83A induction of calcium mobilisation in CHO cell lines.

FIG. 4. Dose response of U83A induction of calcium mobilisation in CCR1, CCR4, CCR6 and CCR8-CHO cell lines. Relative fluorescence units are shown (RFU), and the results performed in triplicates with standard deviation shown. Activities are compared to background on CHO parent cells and low or negative activities on CXCR1, CXCR2 and CCR2-CHO cell lines. No activities at 1 nM or 100 nM U83A-Npep are equal to base-line levels with negative control vehicle buffer only.

Figure 5:
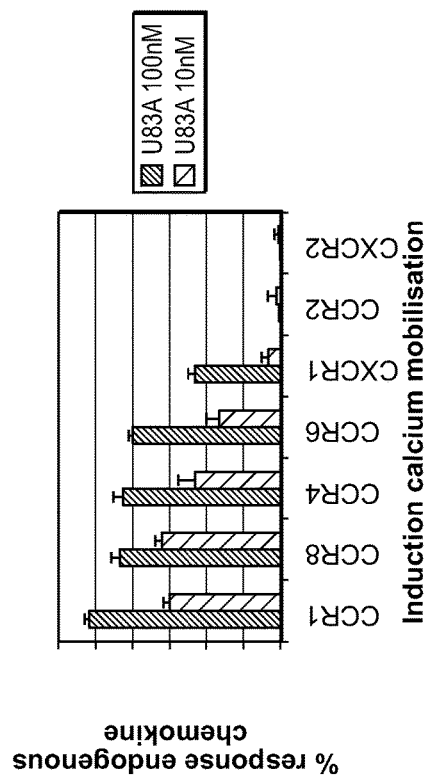
FIG. 5 shows U83A induction of calcium mobilisation in CHO cell lines in comparison to endogenous ligands.

FIG. 5. U83A induction of calcium mobilisation in CCR1, CCR4, CCR6 and CCR8-CHO cell lines in comparison to reactivity to endogenous ligands. Expressed as percentage of maximal response of chemokine induced calcium mobilisation in CHO cells expressing cellular chemokine receptors indicated with Mip1a to CCR1, MDC to CCR4, MIP3a to CCR6, 1309 to CCR8, IL-8 to CXCR1, MCP1 to CCR2, IL-8 to CXCR2. CCR2 and CXCR2 at U83A 100 nM not plotted as although they have values significantly above the vehicle only background they are indistinguishable from background responses on the CHO parent cell line (see FIG. 2). Base-line with vehicle only values subtracted.

Figure 6A:
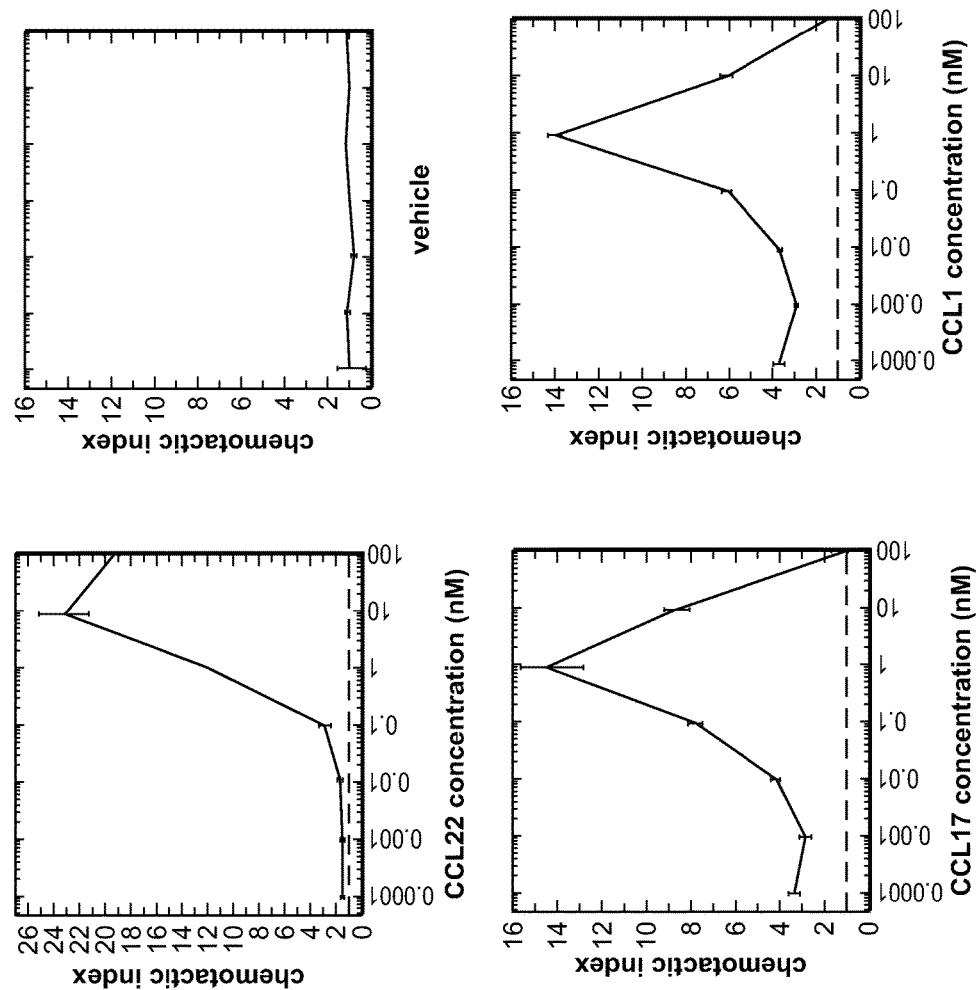
FIGS. 6A-6B show chemotaxis of HUT-78 cells to U83A.
Figure 6B:
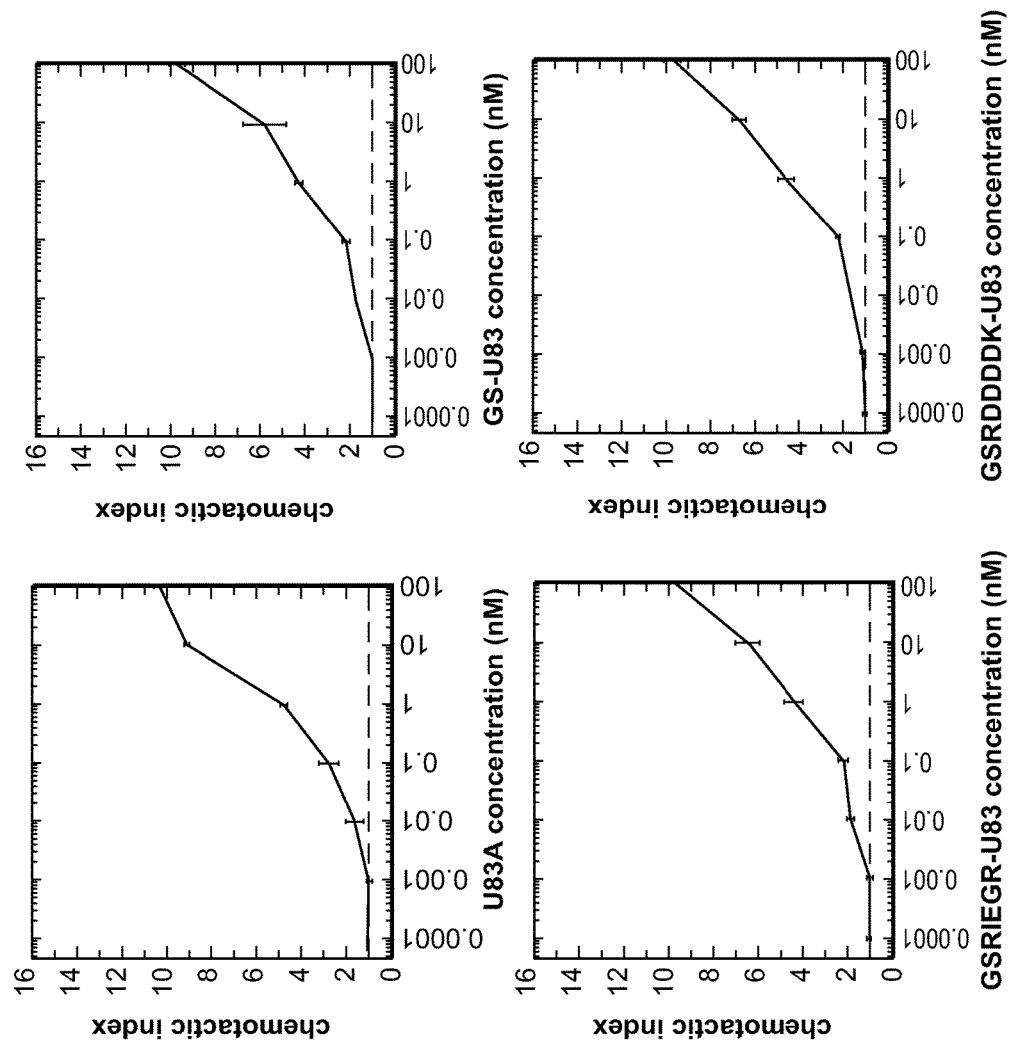

FIG. 6. Chemotaxis of HUT-78 T-lymphocyte cells showing responses to U83A and variants compared to endogenous human chemokine ligands, the CCR4-specific CCL22 and CCL17, the CCR8-specific CCL1 (A-B). Also shown is the negative control of replicates of cells treated only with ligand-free buffer (vehicle). A dose response is indicated showing reactions with ten fold serial dilutions of concentrations from 0.0001 to 100 nM. Error bars are shown for results repeated in triplicate.

FIG. 7. Competition by U83A and variants of chemotaxis induced by human endogenous ligands CCL22 on CCR4 or CCL1 on CCR8. Hut78 cells were pre-incubated for 30 min with vehicle only or 100 nM U83A, GS-U83A, GSRDDDDK-U83A or GSRIEGR-U83A, then treated with maximally responsive endogenous chemokine concentrations of 10 nM CCL22 (for CCR4) shown in A, or 1 nM CCL1 (for CCR8) shown in B, as indicated. Endog=endogenous.

Figure 7A:
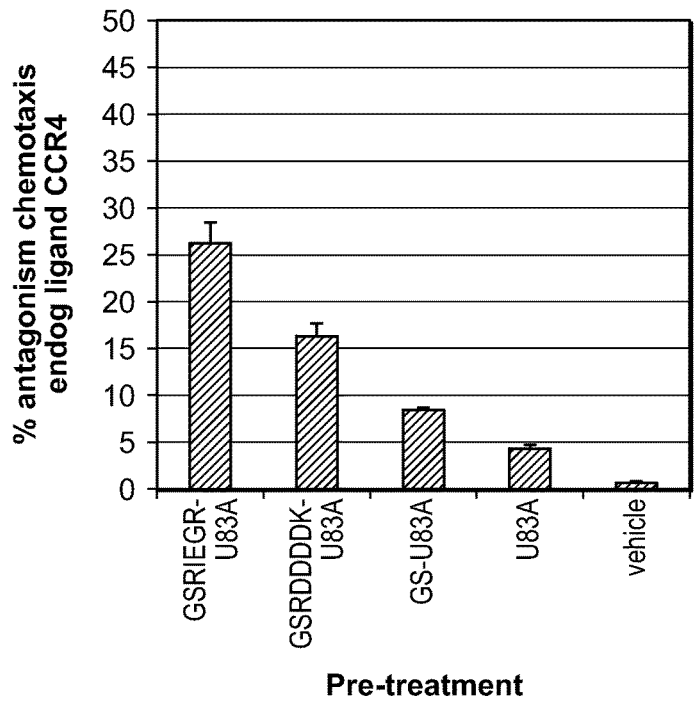
FIGS. 7A-7B show antagonism of chemotaxis by U83A on HUT-78 cells.
Figure 7B:
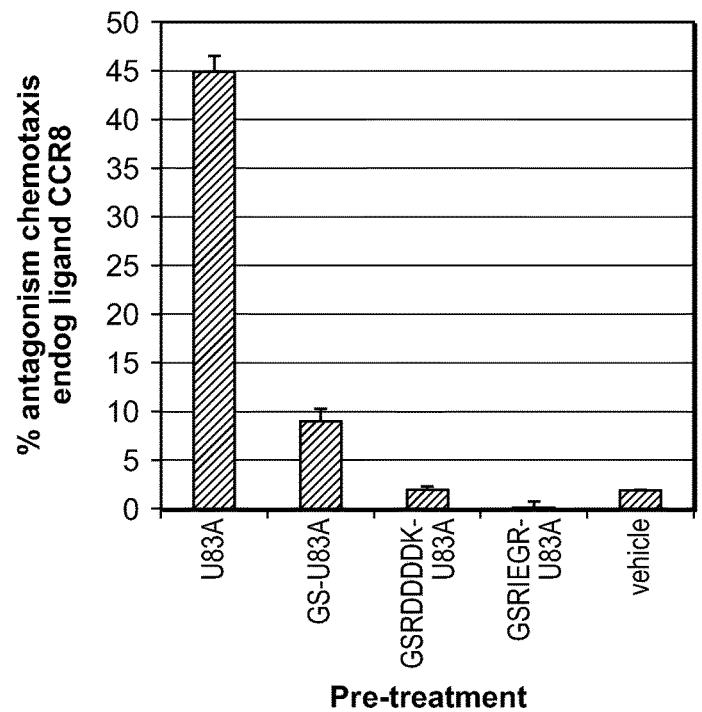
Figure 8:
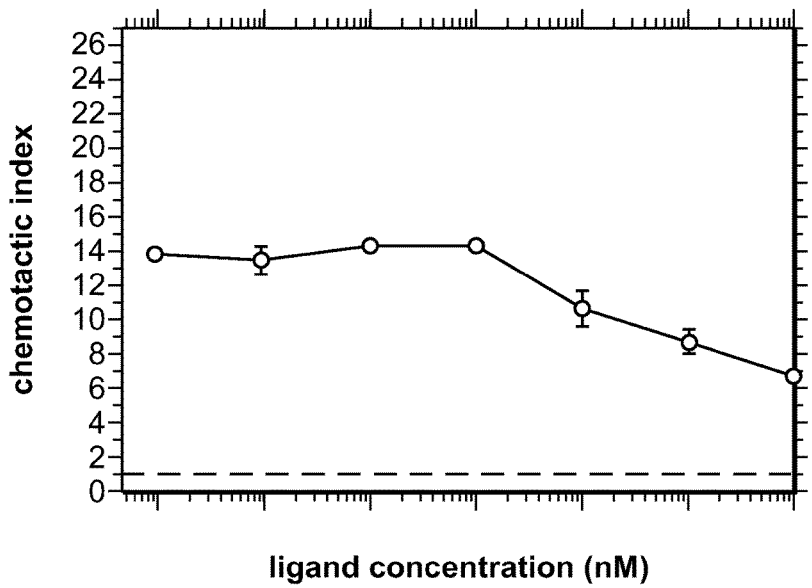
FIG. 8 shows dose response of antagonism by U83A on chemotaxis induced by endogenous ligand for CCR8.

FIG. 8. Dose response of competition effect by U83A on chemotaxis induced by endogenous ligand (CCL1) for CCR8. Competition was shown from 1 nM. The N-terminal variants only showed competition at the highest concentration tested, 100 nM, against CCL17 induced chemotactic responses of CCR4 CHO cells (see FIG. 7) with a marginal effect from 100 nM of GS-U83A on CCL1 induced CCR8 chemotaxis. Error bars are from results repeated in triplicate.

Figure 9:
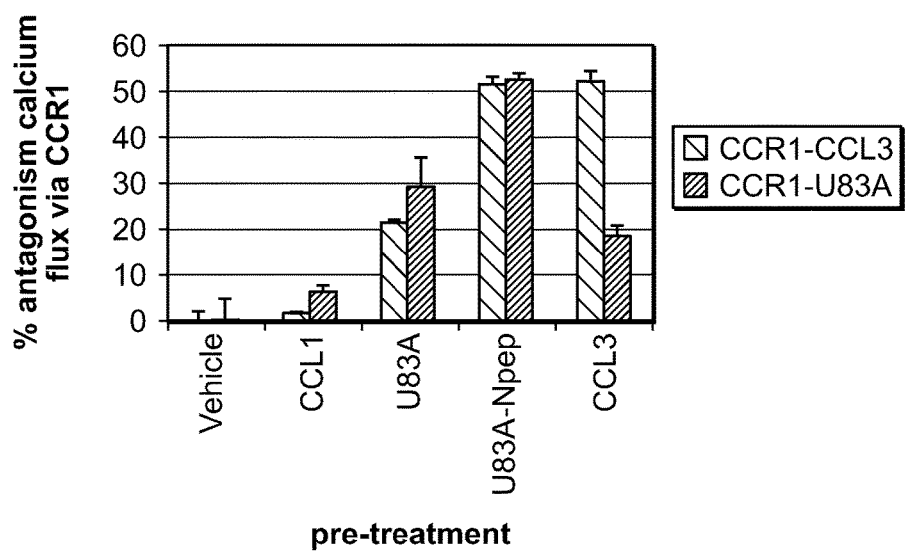
FIG. 9 shows antagonism by U83A and U83A-Npep of CCR1 mediated induction of calcium mobilisation.

FIG. 9. Antagonism by U83A and U83A-Npep of CCR1 mediated induction of calcium mobilisation by U83A (GSR-IEGR-U83) or endogenous ligand CCL3. CCR1-CHO cells were pre-treated with 100 nM of endogenous chemokine ligand CCL3, or U83A or U83A-Npep. Negative controls were the non-binding CCL1 or the vehicle buffer without any chemokine. Then the pre-treated cells were stimulated with the endogenous ligand CCL3 or the viral chemokine U83A as indicated. The maximum peak of calcium flux induced as measured in RFU was expressed as a percentage of inhibition of the response from pre-treatment only with buffer. The results show CCL3 antagonises induction of calcium mobilisation by U83A or is competed out with pre-treatment also with CCL3; U83A antagonises induction of calcium mobilisation by both U83A or CCL3; U83A-Npep antagonises induction of calcium mobilisation induced by U83A or CCL3. U83A-Npep blocks CCL3 induced responses as efficiently as pre-treatment with the endogenous ligand. Negative control CCL1 does not antagonise calcium mobilisation induced by CCL3 or significantly by U83A. All experiments were performed in triplicate and error bars indicated.

Figure 10A:
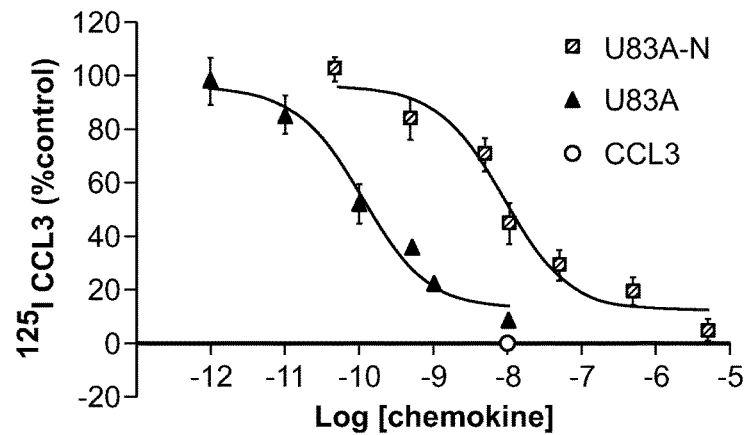
FIGS. 10A-10C show U83A, U83A-N and U83A-Ndel competition binding assay.
Figure 10B:
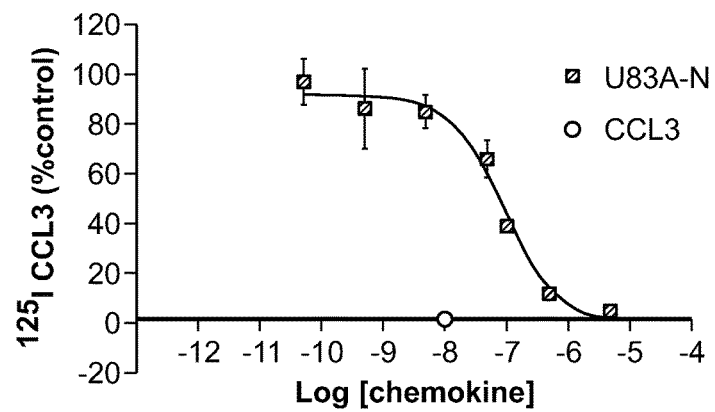

FIG. 10. U83A, U83A-N and U83A-Ndel competition binding assay: Competition binding assays performed, as described in Material and methods, on cells expressing CCR5, (A) U373-MAGI-CCR5E, (B) PBMCs and (C) COS-7 CCR5, using 166 μM $^{125}$I-CCL3 as a tracer and increasing concentration of unlabelled U83 forms as competitor. The data are expressed as a percentage of the maximum bound iodinated chemokine, determined in absence of cold competitor. Total displacement was obtained by 10 nM CCL3 (•). Each point represents mean values±standard deviations of triplicates. EC50 values obtained using U373-MAGI-CCR5E cells were for U83A $1.1 \times 10^{-10}$ M, for U83A-N (U83A-Npep) $8.3 \times 10^{-9}$ M, and for PBMC for U83A-N $9.2 \times 10^{-8}$ M.

Figure 11:
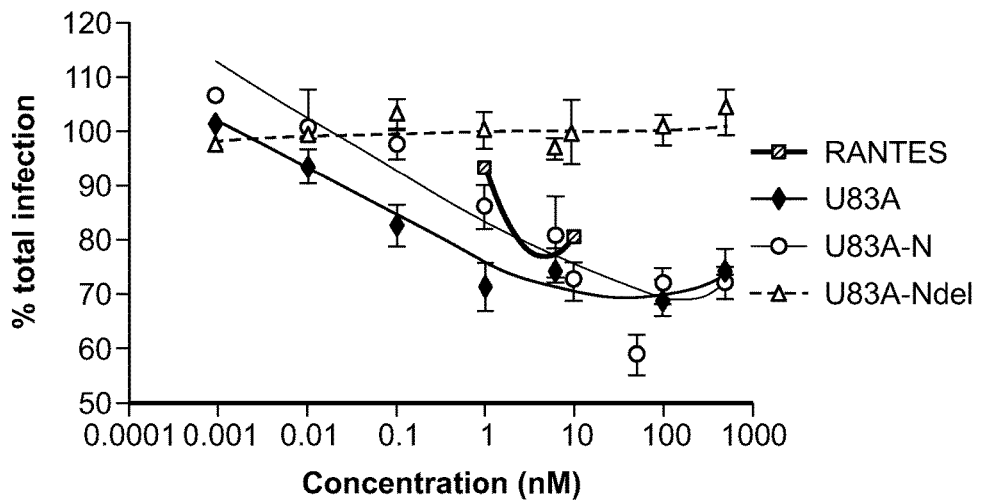
FIG. 11 shows suppression of CCR5-tropic HIV-1 infection by different forms of U83 and RANTES in human U373-MAGI-CCR5E cells.

FIG. 11. Suppression of CCR5-tropic HIV-1 infection by different forms of U83 and RANTES in human U373-MAGI-CCR5E cells. U83A-N and U83A inhibit HIV-1 foci of infection in the same range of concentration than the positive control RANTES. The small form U83A-Ndel did not change the infectivity of HIV. Results (means±SD) are representative of independent experiments.

Figure 12:
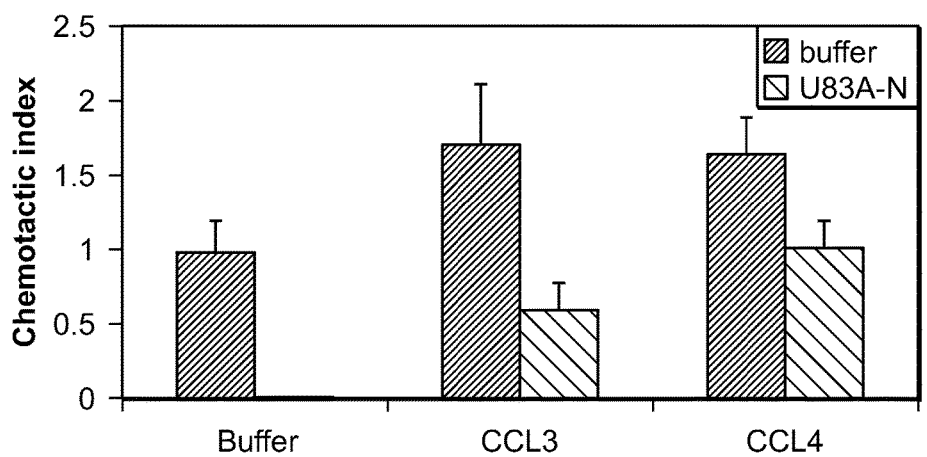
FIG. 12 shows U83A-N blocks CCL3 (A) and CCL4 (B)-elicited ex vivo human PBMC chemotaxis.

FIG. 12. U82A-N blocks CCL3 and CCL4-elicited ex vivo human PBMC chemotaxis. After purification and calcein labelling, cell samples were pre-incubated for 5 minutes with U83A-N at the indicated concentrations. Then, a 5 μm filter was loaded with $5 \times 10^5$ cells and transferred to a 96-well CHEMOTX® plate containing 10 nM CCL3 or 100 nM CCL4 in 30 μl of buffer per well. After 1 h of incubation at 37° C. and 5% $CO_2$, the cells on the upper part of the filter were removed and the cells on the filter and in the well were counted by a spectrofluorimeter.

Figure 13A:
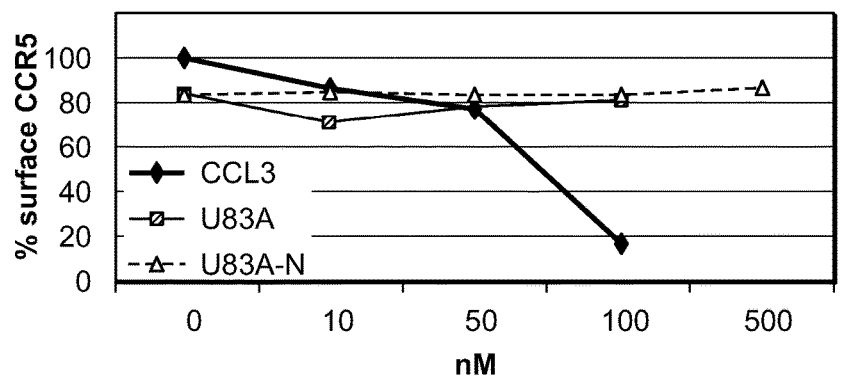
FIGS. 13A-13C show CCR5 is rapidly induced by CCL3 but not by U83A or U83A-N.
Figure 13B:
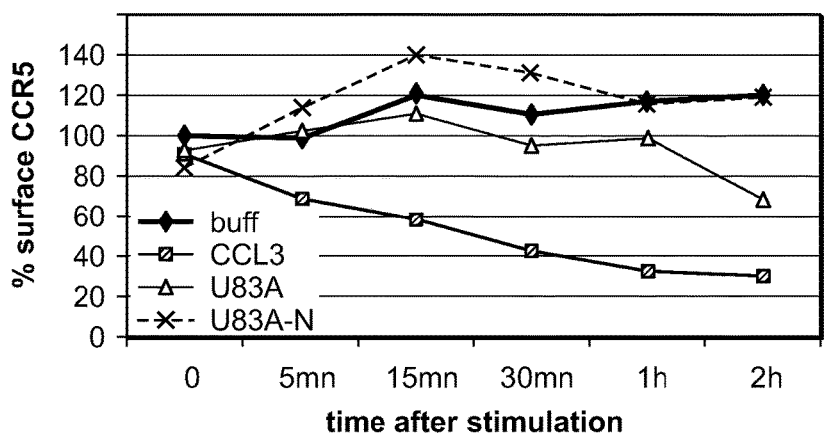
Figure 13C:
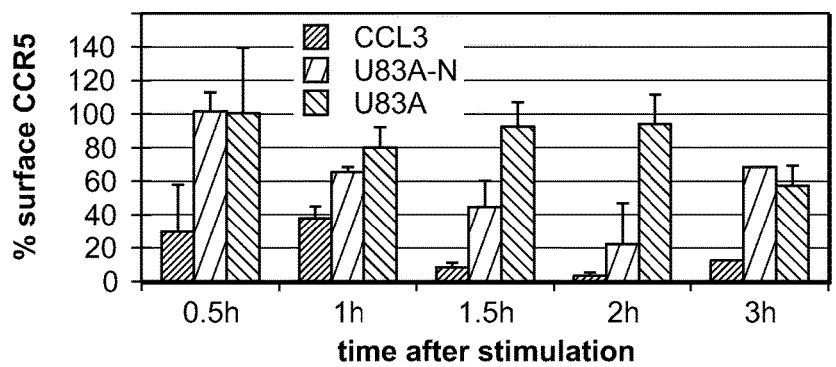
Figure 14A:
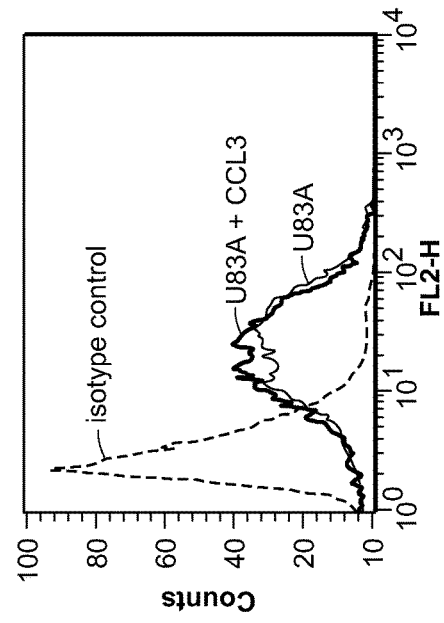
FIGS. 14A-14D show U83A and U83A-N inhibition of CCR5 internalisation induced by CCL3.
Figure 14B:
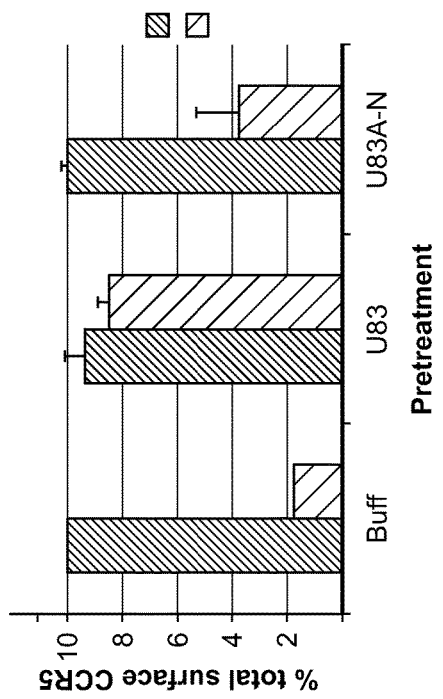
Figure 14C:
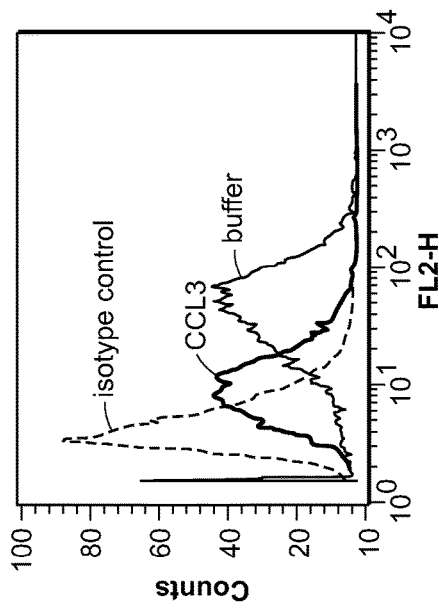
Figure 14D:
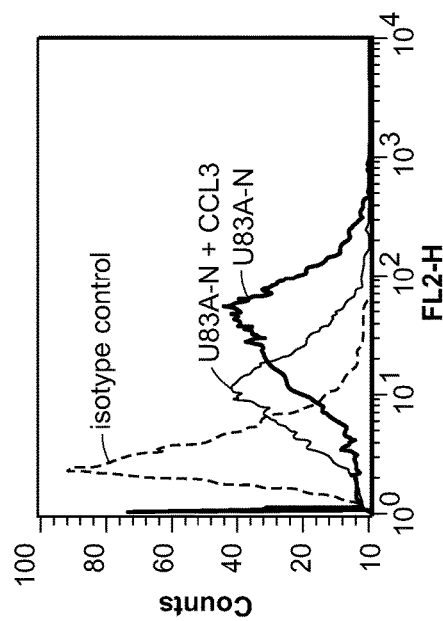

FIG. 13. CCR5 is rapidly induced by CCL3 but not by U83A or U83A-N. Cell surface expression of CCR5 was monitored by FACS in presence of various concentrations of CCL5 and/or U83A and U83A-N at various times. (A) Dose-effect of CCL5, U83A and U83A-N on U373-MAGI-CCR5E CCR5 surface expression after 5 minute incubation. Results shown are representative of 3 independent experiments. (B) Kinetic of CCR5 internalisation over 2 hour induced by 50 nM CCL5, 100 nM U83A or U83A-N. (C) Quantification of CCR5 internalisation inhibition by U83A and U83A-N. Internalisation induced by 100 nM CCL3 inhibition was tested at different concentrations. Results shown are representative of 3 independent experiments.

FIG. 14. U83A and U83A-N inhibition of CCR5 internalisation induced by CCL3:

(A-C) Effect of different chemokines stimulations on receptor internalisation: U373-MAGI-CCR5E cells were treated with 100 nM CCL3, 50 nM U83A, 100 nM U83A-N alone or in combination or medium alone as a reference of basal level of CCR5 expression. The decrease of surface receptor expression was detected by CCR5 specific antibody, before chemokine addition (open histograms, dark black line) and after a 5 minutes chemokine incubation (open histograms, grey lines) compared with the isotype control (dashed lines). D. Summary of effects of preincubation of cells with 50 to 100 nM U83A or 100 to 500 nM U83A-N followed by stimulation with 100 nM CCL3 (representative of two experiments in duplicate).

Materials and Methods
Construction of GST-U83 Expression Plasmids

The U83 gene was amplified by PCR from viral DNA using three different primer pairs to give rise to three different constructs. All three forward primers added a 5' BamHI site to the U83 sequence, and the reverse primer (R83INT) added a 3' EcoRI site to the sequence for directional ligation of the U83 gene into the pGEX-2T plasmid and transformed into *E. coli* strains DH5α then the protease deficient strain BL21 (AMERSHAM BIOSCIENCES). Primers DD3 and R83INT were used to make pU83GST (containing a thrombin recognition site). Primers DD11 and R83INT were used to make pU83GSTEK. An enterokinase recognition site was inserted 5' to the chemokine sequence and the thrombin recognition site provided by the plasmid. Primers FXa and R83INT were used to make pU83GSTXa. A factor Xa recognition site was inserted 5' to the chemokine sequence and to the thrombin recognition site provided by the plasmid. The U83 insert was sequenced from these plasmids using primers DD7 and DD12.

```
Primer sequences:
SEQ ID NO 9:
DD3: 5' TTGGATCCTTTATATGTAGTTCCCCCGAT 3';

SEQ ID NO 10:
DD11: 5' TCGGGATCCCGTGATGATGATGACAAATTTATATGTAGTT

CCCCCGAT 3';

SEQ ID NO 11:
FXa: 5' TCGGGATCCCGTATCGAAGGTCGTTTTATATGTAGTTCCCC

CGAT 3'

SEQ ID NO 12:
R83INT: 5' CTTCGAATTCTTTCATGATTCTTTGTCT 3';

SEQ ID NO 13:
DD7: 5' CCGGGAGCTGCATGTGTCAGAGG 3';

SEQ ID NO 14:
DD12: 5' AACGTATTGAAGCTATCCCAC 3'.
```

Expression and Purification of Recombinant U83, Native and Modified Forms.

U83A and N-terminally modified forms were purified using the GST system as described (19)(AMERSHAM BIOSCIENCES). Briefly, a single colony for each plasmid transformed BL21 *E. coli* (pGEX-2T parent plasmid, and the recombinant U83-containing plasmids pU83GST, pU83GSTEK and pU83GSTXa) was picked, used to inoculate 10 ml of LB medium (containing 100 µg/ml ampicillin), and grown overnight in a 37° C. shaking incubator. Five (5) ml of that culture was then used to inoculate 500 ml of LB-ampicillin medium and cultured to 0.5 OD600. 0.1 mM IPTG was added to induce expression for 3.5 h, then bacteria were pelleted and re-suspended in 16 ml STE buffer (10 mM Tric-HCl, 150 mM NaCl, 1 mM EDTA pH 8.0) at 4° C., then brought to 1.5% N-lauroylsarcosine, followed by cytolysis by sonication. The sonicate was centrifuged, and clarified supernatant was filtered through 0.45 µm then 0.22 µm PVDF filters (FISHER) and added to 1 ml of a glutathione SEPHAROSE® 4B bead slurry in STE with 1.5% lauroylsarcosine (AMERSHAM BIOSCIENCES) then mixed at 4° C. for 1 h. The mixture was then decanted into a 10 ml polypropylene column for batch chromatography (PIERCE) and washed with 20 ml STE buffer with 1.5% lauroylsarcosine. Beads were washed with 8 ml buffer A containing 0.15 mg/ml denatured proteins from *E. coli* BL21 (BL21 proteins). The BL21 protein wash was required to remove a 70 kDa co-purifying bacterial protein, presumed to be the bacterial chaperone dnaK, which recognizes foreign (non-*E. coli*), partially folded, or misfolded proteins in *E. coli* as described (Rial, D.V. et al. 2002; Yu-Sherman, M. and Goldberg, A.L. 1992 and as described for the AMERSHAM GST system). Beads were then washed with 20 ml STE buffer (containing 1.5% lauroylsarcosine) and bound protein was eluted with 8 ml STE, 1.5% lauroylsarcosine +10 mM reduced glutathione, pH 9.0. The eluate was concentrated by centrifugation in a VIVASPIN20® centrifuge (VIVASPIN, UK) then dialysed against PBS using SPECTRAPOR 2.1® membranes (SPECTRUM LABORATORIES), with a 15 kDa cut-off. Quantitation was by Bradford assay (BIO-RAD), followed by cleavage using thrombin to give GS-83A, or protease site modified N-terminal variants GSRDDDDK-83A or GSRIEGR-83A, enterokinase or Factor Xa sites respectively. To derive native U83A enterokinase, Factor Xa was used on the pU83GSTEK or pU83GSTXa derived proteins, respectively. 1.2 mg fusion protein, 60 units thrombin (60 µl in PBS, AMERSHAM), in 2 ml PBS was incubated at 4° C. overnight. For enterokinase digestions, 1.2 mg fusion protein was mixed with 6.4 units of EKMax™ enterokinase (INVITROGEN) in 50 mM potassium phosphate, 500 mM NaCl, 50% glycerol Ph 8.0 diluted in 2 ml PBS with EKMax™ enterokinase reaction buffer (50 mm Tris-HCl, 1 mM $CaCl_2$, 0.1% TWEEN 20 detergent pH 8.0), incubated at 4° C. overnight. For Factor Xa cleavage, 1.2 mg fusion protein, 6.4 units Factor Xa (6.4 µl, AMERSHAM), in 2 ml PBS was incubated at 4° C. overnight. Digestions were followed by analyses by SDS-PAGE and/or separated by RP-HPLC.

Sodium Dodecyl Sulphate Gel Electrophoresis (SDS-PAGE) and Western blotting.

GST samples were analysed using tricine SDS sample buffer (450 mM Tris-HCl, 12% glycerol, 4% SDS, 0.0075% Coomassie blue, 0.0025% phenol red pH 8.45), tricine running buffer (100 mM Tris base, 100 mM tricine, 0.1% SDS pH 8.3) and precast NOVEX® 10% tricine gels (INVITROGEN). Gels were stained using Coomassie blue or a SILVERXPRESS® kit (INVITROGEN).

For western blots, GST samples were blotted from electrophoresed gels using the XCell-II™ Blot Module with the NOVEX® XCELL SURELOCK® mini cell. Gels were blotted for 1 hour at 25 volts constant in tris-glycine transfer buffer (12 mM Tris base, 96 mM glycine pH 8.3) supplemented with 10% methanol, then blocked in 5% milk (Marvel) in PBS, washed in PBS-T (0.1% TWEEN 20 detergent), and then probed with an anti-GST primary antibody (AMERSHAM BIOSCIENCES cat. 27-4577-01, raised in goats), diluted 1/10,000 followed by the secondary antibody (donkey-anti-goat-HRP, PROMEGA, cat V8051) also diluted 1/10,000. Alternatively, blots were probed with rabbit anti-U83 peptide antibody (kindly donated by G. Campadelli-Fume, University of Bologna), diluted 1/10,000 in PBS-T followed by the secondary antibody (goat-anti-rabbit-HRP, PROMEGA, cat W4011) also diluted at 1/10,000, then washed in PBS-T, and then incubated with enhanced chemi-luminescence reagent (ECL PlusTM kit, AMERSHAM BIOSCIENCES). The blot was exposed to HYPERFILM® ECL film.

Reversed-Phase High Pressure Liquid Chromatography (RP-HPLC) Isolation and Purification.

Fusion protein and cleaved native or modified U83A were purified by reversed-phase HPLC using a RESOURCE™ RPC 3 ml column (15 μm polystyrene/divinylbenzene beads) and ÄKTAEXPLORER (AMERSHAM BIOSCIENCES). Protein was acidified to approximately pH 2.5 with trifluoroacetic acid (TFA) to 0.1% (v/v), and 2 ml was loaded onto the column at 2 ml/min and eluted using a buffer gradient with fusion protein eluting in 50.4% acetonitrile. Fractions were lyophilised and stored at −20° C.

Protease-cleaved native U83A chemokine and U83A N-terminal peptide were eluted in 45% acetonitrile and fractions were lyophilised and stored at −20° C. The GST fusion proteins purified by RP-HPLC were re-suspended in PBS (endotoxin certified) and quantitated by Bradford assay using BIO-RAD protein detection reagent and BSA standards (20)(BIO-RAD). Samples of the native U83 chemokine (and N-terminal variants) were re-suspended in water and quantitated by UV spectroscopy at 280 nm with extinction coefficients calculated for each U83A variant as described (21). Resuspended and renatured chemokines in PBS were stored with 0.1% BSA (SIGMA fraction V, endotoxin certified) at −20° C. Endotoxin testing using LAL assay (limulus amebocyte lysate) showed levels lower than 1.0 units per microgram, equivalent or lower than commercially supplied human chemokines.

Cell Lines, Culture and Chemokines

Every cell line used was certified mycoplasma-free at all times.

COS-7 cells were obtained from ECACC. U373-MAGI-CCR5E cells were obtained from the AIDS Research and Reference Reagent Program, Division of AIDS, NIAID, NIH donated by Dr. Michael Emerman (95). Cell lines were maintained in Dulbecco's modified Eagle's medium containing 10% fetal bovine serum, 2 mM L-glutamine, 1 mM sodium pyruvate, 50 units/ml penicillin, and 50 μg/ml streptomycin supplemented with 1 μg/ml Hygromycin B (SIGMA) for stably transfected U373-MAGI-CCR5E cell lines. COS-7 cells were transfected with pCDNA3-expressing CCR1, CCR2 or CCR5 (University of Missouri-Rolla cDNA Resource Center, Rolla, MO) using LIPOFECTAMINE® reagent 2000 (INVITROGEN Life Technologies) following the manufacturer's protocol. Primary human peripheral blood mononuclear cells (PBMC) were obtained from healthy adult volunteers by centrifugation of EDTA anticoagulated blood over a HISTOPAQUE® reagent cushion (SIGMA-ALDRICH). Mononuclear cells were collected from the interphase, washed three times in phosphate-buffered saline (PBS), and used immediately for assays.

Chemokines CCL3/MIP-1α and CCL4/MIP-1β were purchased lyophilized from R&D SYSTEMS, resuspended and renatured in PBS 0.1% BSA (fraction V, endotoxin certified; SIGMA-ALDRICH). Viral chemokines U83A-GS, U83A-N were produced as described previously (89). U83A-Ndel, corresponds to the 17 first N-terminus amino acids of native U83A and was synthesized (SIGMA Genosys).

THP-1 monocyte cell line (derived from monocytic leukemia) (22), K562 human lymphoblasts (from chronic myelogenous leukaemia) (23) and HUT-78 T lymphoblasts of inducer/helper phenotype (from cutaneous T lymphoma, Sezary patient) (ATCC) (24) were all cultured in RPMI without phenol red (INVITROGEN) supplemented with 10% foetal calf serum (heat inactivated; INVITROGEN) with 2mM L-glutamine and for THP-1 cell with 0.1 mM β-mercaptoethanol. Cells were used in signalling assays at early log phase between 0.2-0.6 million cell/ml. K562 cells stably transformed with pCDNA3 plasmid or pCDNA3 plasmid expressing HHV-6 U51 gene were cultured as described (25) with 750 μg/ml geneticin G418 (SIGMA). Chinese hamster ovary cells (CHO) were stably transformed with CCR1, CCR2, CCR4, CCR6, CCR8, CXCR1 and CXCR2. The gene expressing human G proteins Ga16 was added to CCR1, CXCR1 and CXCR2 cell lines, while human Gqi5 was added to CCR4, CCR6 and CCR8.

Flow Cytometry

Receptor expression was confirmed by FACS and signalling assays using mouse monoclonal antibodies specific for human chemokine receptors and isotype controls (R&D SYSTEMS) and reading on a Biosciences FACSCAN® with plotting using BD Biosciences CELLQUEST® software. Non-adherent cells were dislodged, and adherent CHO cells were released using 20 mM EDTA pH 8.0. The cells were centrifuged and resuspended in PBS with 2% FCS. 200,000 cells were then pre-incubated either with BSA or human IgG (THP-1), centrifuged and washed in PBS with 2% FCS, then incubated with chemokine receptor antibody or isotype control for 30 min at room temperature. The cells were then centrifuged again, washed in PBS with 2% FCS and resuspended prior to reading on the FACSCAN®.

Human Chemokines

Human chemokine ligands were supplied lyophilized (R&D SYSTEMS), resuspended and renatured as for U83A in PBS 0.1% BSA, with dilutions stored at −20° C. These included CCL1/I309, CCL2/MCP-1, CCL3/MIP1α, CCL4/MIP1β, CCL5/RANTES, CCL11/Eotaxin, CCL17/TARC, CCL19/MIP-3β, CCL20/MIP-3α, and CXCL8/IL-8.

Flexstation® Scanning Fluorometers For Calcium Mobilization Assay

Intracellular calcium mobilization assays were performed using a FLEXSTATION® fluorometer with a 96-well plate reader (MOLECULAR DEVICES) and a FLIPR® Calcium Plus Fluo 3-AM Assay Kit (MOLECULAR DEVICES) as described by the manufacturer. Briefly, $0.8 \times 10^5$ cells per well CHO or receptor expressing cells were seeded into black-plated, clear-bottomed, 96-well plates and incubated overnight at 37° C., 5% $CO_2$. The medium was aspirated off the cells in the 96-well plate and the cells were then washed with FLIPR® buffer (145 mM NaCl, 5 mM KCl, 2 mM $CaCl_2$, 1 mM $MgCl_2$, 10 mM HEPES, 10 mM glucose pH 7.4: made by addition of 8.47 g NaCl, 0.37 g KCl, 0.29 g $CaCl_2$, 0.20 g $MgCl_2$, 2.38 g HEPES, and 1.8 g glucose to a final volume of 1 L water), which was then aspirated and replaced with complete calcium plus reagent A, B FLIPR® buffer containing Fluo-3 and probenecid. The cells were then incubated at 37° C., 5% $CO_2$ for 1 h. The plates were first read in an 'endpoint' assay to determine equivalent loading, with excitation at 485 nm, emission at 525 nm, with a 515 nm cut-off, then read in a 'flex' assay with ligand addition after 20 seconds of equilibration, with a read time of 120 seconds. Intracellular calcium release was plotted as sharp increases in fluorescence immediately after ligand addition, which gradually returned to the basal level of fluorescence. A SOFTMAX® computer program was used to calculate average values for each set of triplicate values, as well as maximum-minimum values for each average concentration. These values were plotted using GRAFIT 32 software (Erithacius Software Ltd, UK), a four-parameter fit was then applied to the values, and EC50 values were calculated.

Transwell Chemotaxis Assay

Cells were fluorescently labelled with calcein using 2.5 µl of re-suspended 5 µg/µl calcein-AM/DMSO in 600 µl in PBS, and 560 µl of calcein-AM was added to 7 ml of cells at $2 \times 10^6$ cells/ml in complete media ($1.4 \times 10^7$ cells total; per 96-well plate) followed by incubation in the dark at 37° C. for 30 minutes. Then 31 µl PBS 0.1% BSA (carrier) or containing chemokines (100 nM to 0.001 nM) were added to the bottom well on the 96-well chemotaxis plate (NEUROPROBE). The polycarbonate filter (5 µm pore) was replaced and 50 µl of labelled cells were added to the top side wells, and the plate incubated at 37° C., 5% $CO_2$ for 2 hours. Cells were aspirated off the top of the chemotaxis plate and replaced with 50 µl of 20 mM EDTA. The EDTA was aspirated off and the plate was read in a Wallac VICTOR2™ 1420 multilabel counter (PERKIN ELMER). Plates were read with an excitation wavelength of 485 nm and an emission wavelength of 535 nm, with 0.1 s interval between reads. Each set was performed in triplicate and standard deviations calculated. Background random migration using only carrier, gave the chemotactic index value of 1. Chemotactic index values thus represent a 'fold-increase' of chemokine directed over the random migration. All values were plotted using GRAFIT 32 software (Erithacus).

Inhibition of HIV Entry by Reduction of Foci of Infection on U373-MAGI Cells

Stocks of HIV-1 strain YU2 were produced by transfecting 293T cells with pYU2 plasmid (AIDS Research and Reference Reagent Program, Division of AIDS, NIAID, NIH from Dr. Beatrice Hahn and Dr. George Shaw) by standard methods. Viral stocks were tittered on U373-MAGI-CCR5 cells by serial dilution.

U373-MAGI-CCR5E cells were seeded $5 \times 10^4$ cells per well of a 48 well plate overnight. The cells were then treated for 30 minutes at 37° C. with appropriate concentrations of chemokine or peptide in 75 µl volume. One hundred Focus Forming Units of HIV YU2 virus was added in a volume of 75 µl and incubated for three hours at 37° C. The cells were then washed three times with PBS and overlaid with 250 µl of media containing the chemokine or peptide at the relevant concentration. After two days the cells were washed once with 500 µl of PBS and fixed with 1% formaldehyde, 0.2% gluteraldehyde in PBS for five minutes before being stained with X-Gal staining solution (PBS, 4 mM potassium ferrocyanide, 4 mM potassium ferricyanide, 2 mM $MgCl_2$ and 400 µg/ml X-Gal). Stained foci of infection were counted. Results are the mean of duplicate wells, expressed as percentages of untreated wells.

Receptor Binding Assays

Binding assays were performed on U373-MAGI-CCR5E, PBMCs or transfected COS-7 cells. After washing in phosphate buffer saline, cells were suspended at $2.5 \times 10^6$ cells/ml in cold binding medium (RPMI 1640, 0.1% BSA, and 20 mM HEPES (pH 7.4). Assays in triplicate contained $2.5 \times 10^6$ cells, 166 µM radiolabeled chemokine (specific activity, 2000 Ci/mM, $^{125}$I-labeled CCL3/MIP-1α AMERSHAM BIOSCIENCES), and diluted concentrations of unlabeled competitor chemokines. After a 2-h incubation on ice, cells were separated from the unbound chemokine by microcentrifugation through a phthalate oil cushion (1.5 parts dibutylphthalate to 1 part bis(2-ethylhexyl)phthalate with bound radioactivity counted with a gamma counter. Data analyses used Prism 0.1.53 software (GRAPHPAD).

Receptor Internalization And Flow Cytometry

U373-MAGI-CCR5E cells were suspended at $5 \times 10^6$ cells/ml in FACS buffer (PBS, 0.1% BSA). Cells were Fc-blocked by treatment with 1 µg of human IgG/$10^5$ cells for 15 minutes at room temperature. They were then incubated for various times, as indicated, at 37° C. and 5% $CO_2$ in the presence or the absence of CCL3 and/or U83A-GS, U83A-N at various concentrations. Stimulated cells were then incubated at 4° C. with FITC-conjugated anti-CCR5 antibody (R&D SYSTEMS) for 30 minutes. After staining, cells were washed 3 times with ice cold FACS buffer and suspended at $5 \times 10^5$ cells/ml in the same buffer after a 15 minute fixation in 4% PFA. The analysis was done using a FACSCalibur flow cytometer (BD Biosciences). Data were analyzed with CELLQUEST® software (BD Biosciences). Relevant IgG (mouse IgG2B) was used as a negative control.

Transwell Chemotaxis Assay

Migration of PBMCs was evaluated using 96-well chemotaxis plate (NeuroProbe). Migration buffer (HBSS (INVITROGEN), 0.1% BSA) supplemented with different concentrations of chemokine was placed into the lower chamber. Cells were resuspended in the same buffer at a concentration of $1 \times 10^7$ cells/ml, and 50 µl of cell suspension was placed onto the upper well. After 90 minutes of incubation at 37° C. in 5% $CO_2$, cells were carefully whipped off and plate was read at 535 nm in a Wallac VICTOR2™ 1420 multilabel counter (Perkin Elmer, USA) with chemotaxis plate filter in situ. Each set was performed in triplicate, and SDs were calculated. Background random migration using only carrier gave the chemotactic index (CI) value of 1. CI values thus represent a fold increase of chemokine directed over the random migration.

Results

Expression, Purification and Identification of Native HHV-6 U83A

Figure 1A:
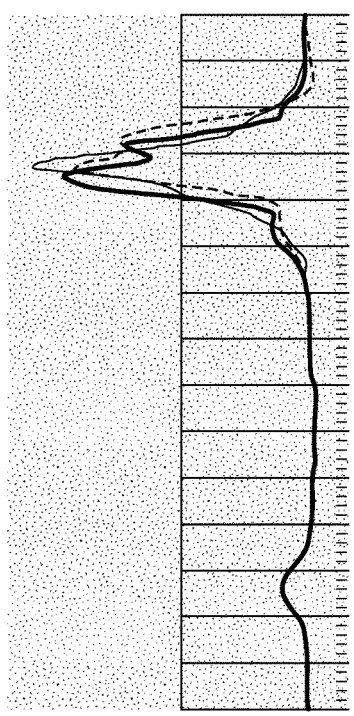
FIGS. 1A-1B show SDS-PAGE (B) and HPLC data (A) of purification of a number of U83A variations.
Figure 1B:
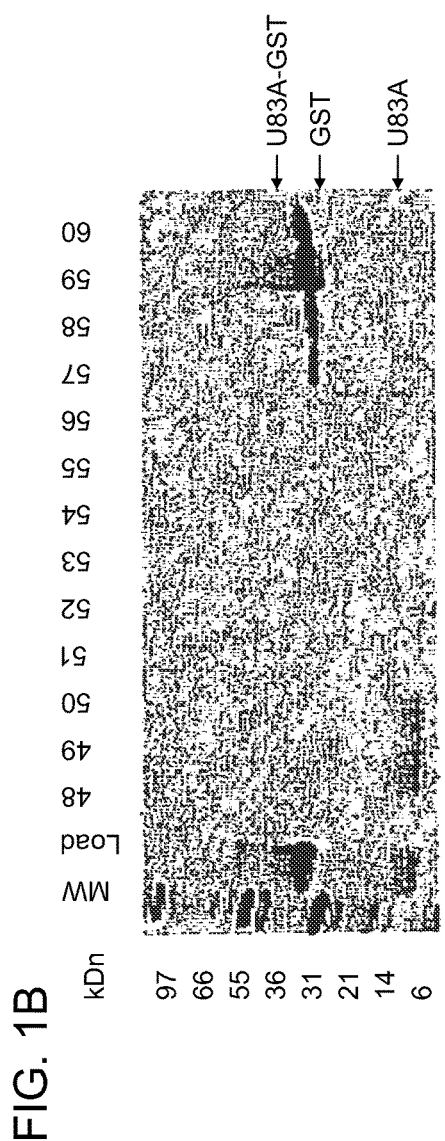
Figure 2B:
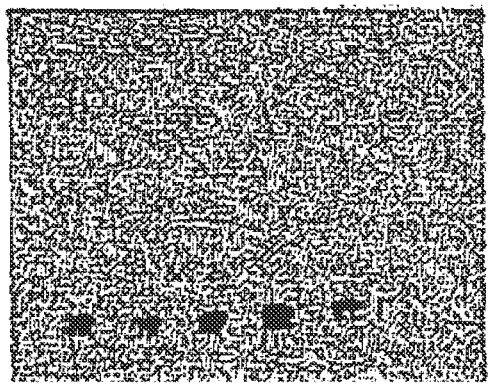
Figure 2C:
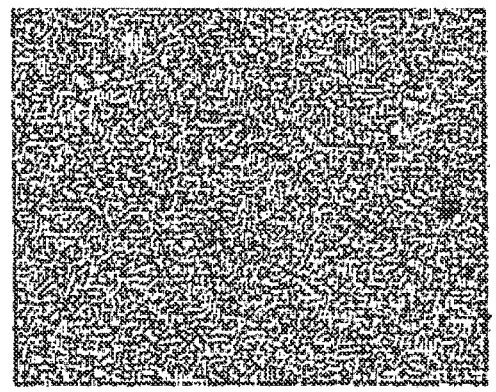

Expression of U83A was examined in HHV-6A strain U1102 infected JJHAN cells (clone of CD4+ Jurkat T leukemic cell line). Both DNA and RNA from cDNA using RT-PCR were sequenced using designated primers from the flanking non-coding regions in the primary genomic sequence (2). The results showed that strain U1102 was polymorphic in this region and an extended version of the gene was identified. Sequencing studies of clinical material also suggested this may be a polymorphic site (not shown). Similar genomic variability has been observed in a homologous region in HCMV encoding a gene product with similarity to betachemokines (11). Both the full length U83A as well as the N-terminal spliced version were produced. The N-terminal spliced peptide corresponding to the N-terminal half of the product, was produced by chemical synthesis, and the full length product together with N-terminal variants by production in E. coli, both were purified using reverse phase HPLC. The mature full length U83A was amplified by PCR as detailed in the methods and expressed as a GST fusion protein in E. coli. The protein was purified by binding to a Glutathionine column followed by elution as described (19). The gene was mutated to include a N-terminal protease recognition sequence for Factor Xa (Xa), or enterokinase (EK) which could cleave at this site resulting in native U83A released from the GST moiety of the fusion protein. Thus three clones were produced one in gGEX2T, one with Xa site, one with EK site. Three versions were produced by thrombin cleavage utilising the thrombin cleavage site encoded in the pGEX2T vector, giving GS-83A, GSRIEGR-83A and GSRDDDDK-U83A. Two native U83A forms were produced using either Xa or EK. These had similar properties, but Xa was more reliable to use, thus this construct was chosen to produce further quantities native U83A. After cleavage the proteins were purified using reverse phase HPLC (RP-HPLC) using a gradient of 40-60% acetonitrile (FIG. 1A). The chemokines separated distinctly from the cleaved and partial cleavage products of the GST fusion as shown in a silver stained SDS-PAGE (FIG. 1B). The synthesized spliced product also purified in similar fractions (not shown). The purified chemokines were identified by Western blot using a U83A peptide specific polyclonal sera (FIGS. 2A, B) which were not recognised by GST specific sera (FIG. 2C), although this was specific for the full length products only as was derived from a peptide covering the splice donor site (FIG. 2B). The N-terminal sequence was confirmed by Edman degradation and sizes were similar to those produced by in vitro transcription translation of both the spliced and full length versions of U83A (26), these also had what appeared as a doublet probably from post-translational modifications such as phosphorylation and there are numerous sites for this modification in the coding sequence. The purified chemokines were dialysed against PBS then freeze-dried for storage. Chemokines were solubilised and re-folded in PBS and stored at −20° C. for less than a month prior to assay.

Hhv-6 U83A Induces Calcium Mobilisation Via Ccr1, Ccr4, Ccr6, And Ccr8

Both full length U83A and U83A-Npep were tested in calcium mobilisation assays for functional chemokine activity. Surprisingly given the positive results with 100 nM U83B-Fc on THP-1 cells and CCR2 transfect L1.2 cells (17, 18), initial results with 100 nM U83A using THP-1 monocytic cell lines with quantitation using individual cell image analyses, only gave isolated responses from single cells in the population while the CCR2 ligand CCL2 induced over 95% of the cell population (not shown). These were cells that were polarised to express CCR2 over CCR1 and CCR2 as shown by flow cytometry, as well as assays using the CCR2 ligand CCL2 in calcium mobilisation and chemotaxis assays. In contrast the K562 pre-erythroid cells which transiently express CCR8 showed potent calcium mobilisation of greater than 95% of the population. In order to follow this further in a defined setting we utilised CHO cells expressing individual chemokine receptors CCR1, CCR2, CCR4, CCR6, CCR8, CXCR1 and CXCR2. CCR3 was also assayed using a scintillation proximity assay (SPA) but U83A and N-terminal modifications (up to 50 nM) did not inhibit induction by endogenous ligand using SPA on CCR3-K562 cells. The results showed that full length U83A could potently and efficiently induce calcium mobilisation via CCR1, CCR4, CCR6 and CCR8 whereas the spliced variant, U83A-Npep, had no effect (FIG. 3). The EC50 for CCR1 and CCR8 were similar to the endogenous ligands with U83A at 9.17+/−0.2 nM and 6.42+/−0.5 nM respectively with CCL3 and CCL1 at 2.75+/−0.9 nM and 3.87+/−0.8 nM respectively. While the EC50s to CCR4 and CCR6 at 8.96+/−0.27 nM and 10.3+/−0.8 nM were at least 10 fold less sensitive than the endogenous ligands at 0.24+/−0.05 nM (CCL17) and 1.27+/−0.03 nM (CCL20) respectively. Comparisons of activities to all the cell lines and the parental cell lines showed significant responses only to CCR1, CCR4, CCR6 and CCR8 (FIG. 4). There were marginal responses to CXCR1 but these were only at relatively high concentrations and diluted out at 10 nM to background levels. Responses to CCR2 and CXCR2 were indistinguishable from background levels on the CHO parental cells. A low activity to a hamster homologue of CCR8 was detected in responses to high concentrations of CCL1 (>100 nM) which was equivalent to these background levels. At 100 nM U83A showed over 100% activity compared to endogenous ligand CCL3, while responses via CCR8 were 85%, CCR4 84%, and CCR6 80%. At 10 nM these dropped to 60%, 65%, 50%, and 35% respectively (FIG. 5). Similar results were found with the N-terminal variants, although the spliced truncated form, U83A-Npep, showed no activity at all concentrations tested (to 100 nM).

HHV-6 U83A Induces Chemotaxis of TH-Like Leukemic Cell Lines

In order to investigate further functional responses to U83A chemotaxis assays were performed with monocytic and T lymphocytic cell lines with defined chemotactic properties and chemokine receptor expression. Chemotaxis assays were first performed using the monocytic THP-1 cells given reactivity demonstrated with U83B-Fc fusion proteins (18). Later results of chemotaxis with CCR2 transfected L1.2 cells using native U83B synthesized form was also consistent as THP-1 cells can express CCR2 (17). In contrast to results with U83B, U83A (0.1-100 nM) induced no chemotaxis with THP-1 cells demonstrated to be polarized for expression of CCR2, by flow cytometry and calcium mobilisation to CCR2 ligands, as well as CXCR4 (not shown). This was consistent with the calcium mobilisation data with U83A using CCR2-CHO cells or THP-1 cells which was indistinguishable from background readings.

Given the reactivity to CCR4 and CCR8 CHO cell lines in calcium mobilisation experiments, chemotaxis assays were performed on a clone of the HUT78 T leukemic cell line which had a TH2 cell phenotype expressing CCR4 and CCR8 (as demonstrated by FACS). Reactions with ligands CCL17, CCL22 and CCL1, respectively, resulted in efficient and potent chemotaxis of this TH2 cell line with maximal efficacy at 1 nM, 10 nM, and 1 nM respectively (FIG. 6). The results showed that U83A also efficiently and potently chemoattracted this cell type. Ranges tested were from 0.0001 to 100 nM, with minimal efficacy at 0.1 nM. At 100 nM, the U83B response was 70% of the response of the endogenous ligands CCL17 (for CCR4) and CCL1 (for CCR8), with 45% of CCL22 (also for CCR4). Chemotaxis normally has a bell shaped curve as shown for the endogenous ligands (FIG. 6), while for U83A, the curve was still rising at 100 nM, thus it is still possible there were more potent reactions at higher concentrations. Interestingly, using N-terminal variants of U83A with N-terminal extensions (encoding the protease recognition sites) similar results were demonstrated (FIG. 6) although most potent responses at 10 nM were shown by the unmodified U83A.

HHV-6 U83A and N-Terminal Variants Inhibit Chemotaxis via CCR4 and CCR8 Ligands

In order to test the specificity of the U83A induced chemotaxis of the HUT78 cells, tests for antagonism were carried out by pre-treatment with U83A prior to assay with the endogenous ligands. The results showed that pre-treatment with 100 nM U83A or the N-terminal variants partially blocked chemotaxis using the maximal effective doses for CCL22 (10 nM) for CCR4 and CCL1 (1 nM) for CCR8. For antagonism of CCR4 responses, a trend for greater antagonism with larger N-terminal extensions was shown, with 25% blocking using pre-treatment with GSRIEGR-U83A (FIG. 7A). While for antagonism of the CCR8 mediated response, native U83A blocked 45% of CCL1 induced chemotaxis whereas N-terminal extensions were not effective, with even GS-U83A only blocking 10% of the endogenous ligand activity (FIG. 7B). Similar results were found in antagonism of calcium mobilisation using a FLIPR based assay with CHO-CCR4 and CHO-CCR8 cells (not shown). Activity against CCL22 induced chemotaxis via CCR4 was only observed at the highest concentration assayed, 100 nM, while a dose response effect could be shown for blocking only by native U83A against CCL1 induced chemotaxis via CCR8 (FIG. 8). Here the concentrations were tested from 0.0001 nM and the minimal effective dose for antagonism was demonstrated from 1 nM.

HHV-6 U83A and Spliced Form U83A-Npep Antagonise CCR1 Signalling

The specificity of the U83A functional interaction with CCR4 and CCR8 was demonstrated by the ability to inhibit effects of respective endogenous ligand. In order to investigate the functional interaction of U83A with CCR1 a similar series of blocking experiments were performed. Here we used the calcium mobilisation assay, as out of receptors assayed, U83A induced signalling via CCR1 most similar to the endogenous ligand (CCL3) in terms of efficacy, 100% of endogenous ligand response, and potency with an EC50 of 9 nM compared to 2.75 nM for endogenous ligand CCL3 (see FIG. 3). This truncated form lacks ability to induce signalling (see FIG. 3), but may still retain the ability to block ligand interactions with the receptor. Given the sensitivity of this assay, we also incorporated an initial characterisation of effects of the U83A spliced truncated form, U83A-Npep. Pre-treatment of CCR1-CHO cells with 100 nM endogenous ligand CCL3 blocked calcium flux by 50%, whereas native U83A partially blocked by 22% of the maximal effective dose of CCL3. Interestingly, the spliced form of U83A, U83A-Npep (at 100 nM), which did not induce calcium mobilisation on its own (FIGS. 3, 4), effectively blocked the CCL3 induced signalling by 50%, similar to that found with CCL3 itself. While reactions with an unrelated chemokine, CCL1 (specific for CCR8), at the same concentration did not block the CCL3 induced response significantly above background (FIG. 9). Similar results were obtained by pre-treatment with the same series of the U83A induced response via CCR1. Here pre-treatment with 100 nM U83A blocked by 30% the subsequent induction with 10 nM U83A, while blocking with 100 nM CCL3 was less effective at 20%. Again the most effective antagonism was shown with pre-treatment with 100 nM U83A-Npep which blocked 50% of the response induced with 10 nM native U83A (FIG. 9). Thus, reciprocal blocking experiments demonstrated the specificity of U83A for CCR1, with most effective antagonism by either the endogenous human chemokine ligand, CCL3, or the viral U83A-Npep.

Receptor Binding Assays

Figure 10C:
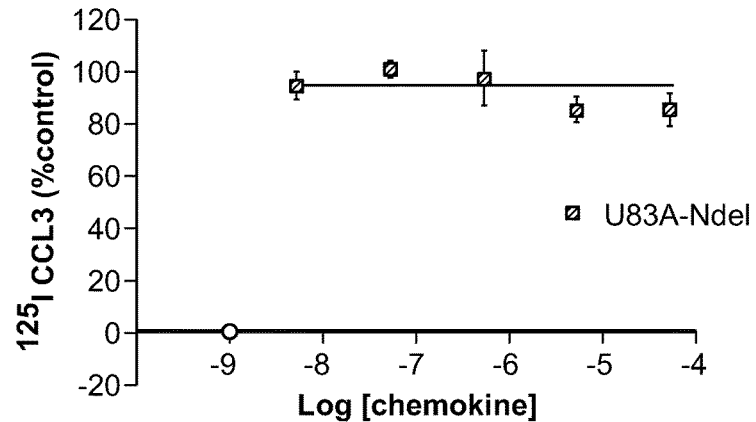

Previous results showed efficient binding of native U83A and the spliced isoform U83A-N on COS-7 cells transiently expressing CCR5 as well as on a monocytic cell line U937, which also expressed CCR1 (89). These interactions were tested here on primary cells and cell types used to assay HIV infection in order to further assess their implications for in vivo interactions and possible inhibition of HIV-1 infection which utilises CCR5 as a co-receptor. First assays were done on U373-MAGI-CCR5E cells which are derived from the U373 astrocytoma adherent cells used for HIV transfection and infection experiments and express the HIV-1 co-receptor CCR5 (95). In competition binding assays against CCR5 ligand Mip1α/CCL3, on U373-MAGI-CCR5E cells U83A showed very high affinity interactions ($IC_{50}=1.1\times10^{-10}$M; FIG. 10) similar to that shown previously for COS-CCR5 cells ($IC_{50}=5.6\times10^{-11}$ M, (89)). The shorter naturally occurring spliced isoform, U83A-N, was also tested on both U373-MAGI-CCR5E and human PBMCs and obtained $IC_{50}$: $8.3\times10^{-9}$M and $9.2\times10^{-8}$ M, respectively, similar to previous values obtained on PMA induced U937 cells expressing both CCR1 and CCR5 ($5.4\times10^{-8}$M) (89). Thus, U83A-N was also a high affinity ligand for CCR5 although with reduced potency compared to the full length U83A. The affinity remains in the same range of efficiency as the human endogenous CCR5 ligands, with full length U83A one of the highest affinity natural ligands reported. The data are specific for CCR5 as U373-MAGI-CCR5E did not express receptors CCR1, CCR2 and CCR8 when checked by Fluorescence-activated cell sorting (FACS) experiments (data not shown). In marked contrast to the data with natural forms U83A and U83A-N, further truncation of U83A-N to make the shorter synthetic peptide U83A-Ndel, resulted in a peptide with no affinity for CCR5 (FIG. 10C). The full length U83A showed the highest affinity interactions with CCR5 followed by U83A-N, while a further truncation was inert, U83A-Ndel. This demonstrates that the binding specificity is in the N-terminal part of U83A (contained in U83A-N), but that stable interactions are provided by the C-terminal half, which is also involved in signalling (89). These interactions are approximately 50 fold more efficient than those with CCR5 described for the KSHV chemokine antagonist shown previously to inhibit HIV-1 infection, vMIPII with some activity by vMIPI, although CCR5 binding has not been demonstrated and vMIPI has been shown a CCR8 agonist (90, 28).

Inhibition of HIV Infection Using Either CCR5 Specific Strain or CCR5 Specific Cell Line As pre-treatment with U83A and the spliced form, U83A-Npep, could block functional responses with endogenous ligand, we sought to investigate other functional activities. Two other viral chemokines, vMIPI and vMIPII, have been shown to effectively block HIV entry by antagonising the chemokine co-receptors. In the case of vMIPII most effective blocking was by strains utilising CCR3 or CCR5 expressed on a glial cell line, while vMIPI could effectively block infection of PBMC by a CCR5 specific HIV strain (27, 28). The antiviral activities of the efficient CCR5 ligands U83A and U83A-N were next assayed in the U373-MAGI_CCR5E cells which displayed high affinity binding with U83A and U83A-N. These cells express β-gal under the control of HIV LTR, which is transactivated by HIV Tat to give an indication of relative virus replication levels. These cells express CD4 and the human chemokine receptor CCR5 on its surface, allowing infection by most primary HIV strains, normally R5 utilising. An R5 HIV strain, YU2, was tested in inhibition assays using CCR5 human chemokine ligand and HIV inhibitor, RANTES/CCL5, as a positive control, and as negative control, U83A-Ndel, the smallest U83A truncation peptide which does not bind CCR5 (FIG. 10). The results show that U83A was more effective than RANTES/CCL5 in inhibiting HIV infection, with U83A-N (abbreviation for U83A-Npep) also effective but with less potency. The estimated EC50 for the HIV inhibitory effects, of 0.1 nM, U83A, and 5 nM, U83A-N, matched the respective affinities for CCR5 and showed up to 50% inhibition at 50 nM (FIG. 11). In contrast, U83A-Ndel, which does not bind CCR5, had no effect on HIV infection.

In order to confirm these results a second entry assay was used. U83A had some activities similar to CCL22 and earlier reports had shown that CCL22 (MDC) was identified as the CD8 T cell secreted soluble activity suppressing HIV (29, 30). Further, some strains can utilise CCR8 as co-receptor (31, 32). However, the main strains for transmission utilise CCR5, and U83A has high affinity for CCR5 as shown above. Thus, HIV infection was assayed using CEM-NKR-CCR5-luc cells which are CEM.NKR-CCR5 cells stably transfected with the luciferase reporter gene under the transcriptional control of the HIV-2 LTR (33). Here, HIV-1 infection is measured by cells responding to Tat expression by producing luciferase followed by quantitation in a luminometer. Both CCR5 and CXCR4 are expressed in this cell line. Since no functional results were found in assays of cells expressing CXCR4 (not shown), experiments were performed using the CCR5 specific HIV strain JRCSF (34). Results showed 93% and 54% reduction of HIV-1 infection using 1 uM GS83A or GSRDDDK-83A, respectively. Furthermore, 5 µM of the splice variant, U83A-Npep, also showed 90% reduction of infectivity. These results were similar to those shown for KSHV vMIPI which showed 80% reduction in infectivity of PBMC by the CCR5 specific strain SL-2 by 100 nM vMIPI or 50% reduction by 100 nM vMIPII on the U87/CD4 CCR5 cell line (27, 28).

Transwell Chemotaxis Assay

In order to further investigate actions of U83A on the normal function of CCR5 in vivo, we tested the effects on CCR5-mediated chemotaxis of ex vivo human donor PBMC. U83A-N was tested as this separates from the signaling U83A (89). The inhibiting activity of U83A-N was tested against CCL3 and CCL4-induced migrations, using a 96-well CHEMOTX® plate assay (FIG. 12). CCL3 and CCL4 are both agonists for receptor CCR5. While CCL3 is also able to activate CCR1, CCL4 is primarily for CCR5. Migratory behaviour of PCMCs, isolated from four separate donors, in the presence of buffer was compared to migratory behaviour after preincubation by U83A-N. U83A-N was able to efficiently block human chemokine-induced chemotaxis via CCR5. Although using the same conditions, U83A-N more efficiently blocked CCL3-induced chemotaxis than CCL4. This is consistent with U83A activity against both CCR1 and CCR5, thus affecting more cell types. However, the inhibition against CCL4 shows U83A is also CCR5 specific and can block receptor function. Thus, U83A binding can inhibit normal human chemokine-mediated functions in chemotaxis of CCR5 cells.

Receptor Internalisation

The next sets of experiments investigate the mechanism of action of U83A mediated inhibition of chemotaxis and HIV infection. The CCR5 binding studies showed that U83A and U83A-N effectively displaced binding of endogenous human chemokine ligands. Thus, virus chemokine inhibition of CCR5 mediated chemotaxis or HIV infection could be by blocking binding, or alternatively (or in addition) it could be by affecting CCR5 cell surface expression. In order to investigate whether infection or chemotaxis attenuation involves modulation of CCR5 cell surface expression, we examined receptor internalisation following ligand binding. First, the expression of CCR5 on U373-MAGI-CCR5E was monitored before and 5 minutes after treatment with various concentrations of endogenous human chemokine ligand CCL3 or the viral chemokines U83A and U83A-N. As shown in FIG. 13-A, CCL3 (at 100 nM) markedly decreased the level of CCR5, as expected for an agonist, whereas the viral chemokines did not induce any internalisation of CCR5 up to concentrations of 500 nM. This was further tested over increased time intervals. Here, after 30 min exposure to endogenous human chemokine most of the CCR5 is internalised whereas there is minimal effect by the viral chemokines even up to 2 hours. In extension to 3 h there was gradual internalisation of CCR5 by U83A, suggesting affecting recycling of CCR5. There is an intermediate effect by U83A-N, with delayed internalisation. Thus while human chemokine ligand CCL3 efficiently and rapidly induced internalisation as described previously (97), U83A did not induce any internalisation of CCR5, and U83A-N showed a delayed internalisation by comparison with CCL3 induced internalisation. The short form U83A-N failed to induce any internalisation at the tested dose (100 nM). 2 h after stimulation 100 nM U83A started to cause receptor internalisation (44%) suggesting the mobilisation of a different internalisation pathway than the one induced by CCL3 to internalize CCR5 (43% internalisation after a 5 minute incubation).

Next tested were the effects of blocking the human agonist induced CCR5 internalisation. Here, U83A and U83A-N pre-treatment of cells before stimulation by 100 nM CCL3 prevent CCR5 internalisation (FIGS. 14 B, C, D) Inhibition of CCR5 internalisation was more efficient when the full length form of U83A, 10-50 nM, which showed complete blocking of CCL3 (100 nM) induced internalisation of CCR5. While, only 50% inhibition was shown using 100-500 nM of the truncated, spliced form, U83A-N. Thus, U83A and U83A-N displace endogenous human chemokine ligands from binding CCR5 thereby preventing CCR5 internalisation and blocking human chemokine directed chemotaxis as well as preventing utilisation of CCR5 as a co-receptor for HIV. The effects correlate with the respective binding affinities.

Discussion

Properties of HHV-6 U83A, N-Terminal Variants and Spliced Form

These results show that in functional assays using both calcium mobilisation and chemotaxis HHV-6 U83A can function as a potent, selective chemokine agonist with broad betachemokine reactivities to CCR1, CCR4, CCR6 and CCR8, while interaction with CCR5 demonstrated up to a log higher affinity than human endogenous ligands at 0.1 nM. Binding displacement studies also show high-affinity binding for CCR1 and CCR5 at sub-nanomolar levels. The most potent responses were to CCR1, CCR5 and CCR8 which were similar to or exceeded those found for the endogenous human ligands. The sensitivity was CCR1, CCR5>CCR8>CCR4>CCR6. Potent responses were demonstrated by minimal effective doses shown for CCR8 2.5 nM, and 7.5 nM for CCR1, CCR4, CCR6 and CCR8 in calcium mobilisation assays and 0.1 nM in chemotaxis assays. Specificity was shown in blocking activities of endogenous ligands in calcium mobilisation and chemotaxis assays. Responses were efficient showing 80-100% compared to endogenous ligands. U83A showed very high affinity binding to CCR5 at 0.1 nM with high affinity to CCR1 at 0.4 nM, while U83A N-pep showed moderate affinity at 50 nM between cell systems, indicating ligand binding in the N-terminal domain of the molecule with C-terminal regions enhancing binding.

We have shown previously that expression of U83 early in infection is modulated by novel cellular splicing which results in the introduction of a stop codon which interrupts in half the chemokine gene after the first set of conserved cysteines (26). The full length version is only produced late in infection after DNA synthesis. Interestingly, the spliced version showed no agonist activity only antagonist activity demonstrated for CCR1 with a fuller description to be described elsewhere. This would be consistent with activity during infection where early in infection the antagonist activity could act in immune evasion protecting the infected cell from immune cell surveillance, whereas late in infection after the virions are produced the agonist properties of the full length chemokine can chemoattract cellular populations for virus dissemination or latent infection.

While only minor differences were found using the N-terminal variants in assays of chemotaxis or calcium mobilisation, there were more marked differences in the antagonism studies of chemotaxis. Here only native U83A was effective in blocking the CCL1 induced chemotaxis via CCR8 whereas the larger N-terminal extensions showed some partial activity in blocking the CCL22 induced chemotaxis via CCR4. This suggests that the sites for interaction are overlapping rather than identical and perhaps the larger N-terminal footprint may be required to block the signalling required for chemotaxis mediated by CCR4, whereas for CCR8 perturbation of the N-terminal region affects its efficiency in blocking the signalling via CCR8.

While we have shown here that U83A appears to have a broad, albeit selective, betachemokine functional profile, with high potency, recent studies on U83B encoded by HHV-6 variant B (17) show a mono-specific CCR2 activity with low potency. This could highlight some of the subtle cellular tropism differences which have been characterised between the strains using leukemic cell lines for cultivation. While both activities could chemoattract monocytic cells through different receptors, U83A could chemoattract a wider range of cell types for further dissemination. Of particular interest are the skin homing T cell properties of CCR4 and CCR8 cells, and in vivo analyses of sites of persistent infection by PCR analyses of biopsy material showed frequent detection of HHV-6A strains at sites in the skin (35) and could explain the wider distribution of HHV-6A strains identified to date, for example higher prevalence in lung and neuronal tissue. The CCR4/CCR8 phenotype of TH2 cells could also contribute to the well defined cellular tropism of HHV-6 for CD4+ T lymphocytes in chemoattracting this cellular population for infection, while all the reactive receptors CCR1, CCR4, CCR6 and CCR8 are present on T lymphocytes.

The observation of functional activities via CCR1 and CCR6 both of which are present in immature dendritic cell types and infiltrating cells in inflammatory lesions in the brain. These have implications in therapeutic applications as discussed below, but also may be consistent with sporadic reports of connections of HHV-6 with multiple sclerosis. Both CCR1 and CCR6 have been implicated in studies of both animal models (EAE) and on human biopsy material. Recent results on HHV-6 have implicated HHV-6A in a subset of patients with MS, as reviewed (5). Furthermore, in studies where comparisons have been made to the closely related HHV-7, although this virus is also neurotropic and like HHV-6 can also be identified as a commensal in the brain, there have been no links of this virus with MS. Interestingly, although most genes are in common between these two Roseoloviruses, strikingly the chemokine gene is deleted in HHV-7 (2) (36). This combined with the functional properties described here for U83A suggests during active infection, U83A is a potential therapeutic target for intervention in MS and further that investigation to inhibit the repression of the novel cellular splicing may prevent its expression and encourage the natural antagonist properties of the U83A-Npep.

Comparisons to Other Viral Chemokines

What properties do U83A and U83A-Npep share with other viral and cellular chemokines? HHV-6A U83A is the only broad potent betachemokine agonist. Currently CCR4, CCR6 and CCR8 are restricted in human chemokine ligands with only two defined for CCR4, CCL17 and CCL22, one for CCR6, CCL20, and one for CCR8, CCL1. CCR6 also interacts with other molecules, the bacterial betadefensins, which are discussed further below. In contrast CCR1 interacts with a range of ligands CCL3, CCL3L1, CCL5, CCL7, CCL14, CCL15, CCL16, CCL9/10 and CCL23. Each of these are restricted to CCR1 with the exceptions of CCL5 which also interacts with CCR3 and CCR5, CCL7 also to CCR2 and CCR3, CCL14 also to CCR5, and CCL16 also to CCR2. Thus, U83A has a unique combination in functional interactions between CCR1, CCR4, CCR6, and CCR8. The cell types these receptors are present on represent a unique array of monocytic (CCR1, CCR8), T lymphocytes (all), TH2 lymphocytes (CCR4, CCR8), immature dendritic cells (CCR1, CCR6) as well as reports on NK, eosinophils and endothelial cells (CCR8) which can all be targets for lytic or latent infection by HHV-6. The fact that passaged virus strains have this gene interrupted suggests that like passaged HCMV strains expression of a betachemokine may not promote or be necessary for in vitro cultivation (11, 13). Of the other viral chemokines described in herpesviruses and poxviruses, vMIPI also has potent agonist activity but this is restricted to CCR8 (28, 37-39) with EC50 for calcium mobilisation of specific CCR8-Y3 cells or IL-2 stimulated primary T cells from 0.1 to 1 nM respectively, and antagonism of the endogenous ligand CCL1 (38). Results for vMIPII, in contrast have been as a broad antagonist activity to CCR1, CCR2, CCR3, CCR5, CCR8, CXCR3, CXCR4, XCR1 and CX3CR1 (27, 40). Isolated reports using primary Eosinophils and TH2 cells have demonstrated agonist activities in calcium mobilisation and chemotaxis assays (28, 41) suggesting other activities or effects of cellular contexts. While vMIPIII has only shown agonist activities of very low potency for CCR4 with chemotaxis of primary TH2 cells only above 100 nM or specific CCR4 transfected L1.2 cells above 500 nM concentrations, with no data on calcium mobilisation (42). In contrast, HCMV encodes a potent alphachemokine, UL146, agonist for neutrophils in calcium mobilisation and chemotaxis with binding to CXCR2 (43). In poxviruses, a potent but selective antagonist for the betachemokine receptor CCR8 was identified which blocked calcium mobilisation and chemotaxis of CCR8-HEK293 and CCR8-L1.2 cells respectively (37, 40, 44, 45). A betachemokine like gene has recently been identified in HCMV (11, 13) but this has not been characterised, while related betachemokine genes in MCMV and GPCMV show selective CCR3 and CCR1 activities respectively, although the GPCMV MIP protein was His tagged and may have altered specificities (14, 15, 43, 46). Restricted chemokine-like activities have been described for other viral molecules encoded by retroviruses including HIV Tat and HIV gp120, both of which appear to Thus, taken together all comparisons to date, HHV-6 U83A alone is a novel viral betachemokine showing potent, broad but selective agonist activities to CCR1, CCR4, CCR6 and CCR8.

Effects on HIV Infection

Given that HIV uses chemokine receptors as co-receptors for infection, chemokines and their altered derivatives have been studied as inhibitory factors to virus entry. In vivo, HIV primarily utilises two receptors CCR5 and CXCR4, which characterise mainly monocytic and T cell tropic lines, although this distinction is not exclusive and some subtypes have not yet displayed progression to utilisation of CXCR4. Further in vitro assays have shown utilisation of other chemokine receptors including CCR8 and CCR4 but much depends on the relative densities of cell surface expression of these receptors (31, 47-49). CCL5 and modified versions are effective inhibitors of HIV-1 infection by preventing entry by utilising the CCR5 coreceptor by R5 utilising strains. These strains appear the most important for both vertical and sexual transmission with combined barriers contributing to this selectivity (91). Additionally, CCR5 has been viewed more favourable to target for HIV inhibition since naturally occurring deletion mutations (i.e., CCR5delta32) are tolerated and give some resistance to infection (92). Further, in some HIV patients, development of CCR5 antibodies correlate with downregulation of the CCR5 receptor cell surface expression and inhibition of HIV infection (93). Although there are antiretroviral combination drugs available which have been effective, they have side effects, are complex to use, do not provide lifelong protection and drug resistance emerges. Thus, there is a need to develop new antiviral therapies targeting other stages of the replicative cycle, including CCR5 (94). Effort has also been directed on developing effective vaccines, which are difficult given the mutability of the selected virus targets and challenges to stimulate effective immunity.

There may be quite distinct effects on HIV by chemokines encoded by HHV-6A and HHV-6B variants, since our studies show U83A from HHV-6A, but not U83B from HHV-6B, efficiently binds the HIV co-receptor, CCR5, effectively displacing the human endogenous ligand RANTES/CCL5, with a log higher affinity, at 0.06 nM, and acts as a potent and efficient agonist (89). This is distinct from other viral chemokine HIV inhibitors which are antagonists (90, 28). Two viral chemokines have been described which have in vitro HIV inhibitory properties. These are KSHV vMIPI and vMIPII, while a third, vMIPIII, in comparative assays has no activity (27, 28, 42). In these studies, a glioma cell line was used, U87, which was transfected with CD4 and different chemokine receptors, then HIV p24 assays performed to monitor infection. All the studies showed using dual tropic strains that infection was most effectively inhibited using 50-200 nM vMIPII on CCR3 expressing cells. In addition, there was also partial activity using CCR5 and CXCR4 (27, 28). Primary PBMC were also used in one report which showed 80% inhibition by 100 nM vMIPII on a CCR5 specific strain SL2 with also 40% or less by vMIPI (28). In these cases as vMIPII is a broad chemokine antagonist, while vMIPI a specific CCR8 agonist which can block endogenous ligand, the mechanisms of action are distinct with more potency displayed by vMIPII.

In the studies shown here, in contrast to the KSHV chemokines, HHV-6 U83A is a potent agonist like vMIPI but unlike vMIPI binds with high affinity to CCR5 and with broad selectivity for other specific betachemokine receptors and can also block action of endogenous ligands, whereas the spliced form U83A-Npep, no longer retains agonist activity, but still can block activity of endogenous ligands. Here, both forms full length and spliced, can efficiently inhibit HIV infection, 93% and 90% respectively in a luciferase indicator entry assay and 50% in a beta-galactosidase indicator entry assay. While N-terminal extensions of the full length appear to compromise activity as also shown in the antagonism assays of CCR8 mediated chemotaxis, thus the longest extension GSRDDDDK-83A shows only partial inhibition at 54% reduced infection. Thus, both forms of U83A or modified molecules may have utility against HIV infection and also raises the possibility that infections or reactivations of HHV-6A may alter, possibly reduce, replication of selected strains of HIV. Certainly, it has been demonstrated that high proviral HIV load in peripheral organs correlates with levels of disseminated HHV-6 DNA detected (50), while with HIV/AIDS progression, HHV-6 viral loads detected in the blood are lowered coincident with depletion of its target cell, the CD4 T lymphocyte (51-53). This depletion in the blood may also enhance HIV replication in other cell types by removal of a natural, albeit viral, chemokine inhibitor.

Possible Applications on Basis of Reactivity with CCR1, CCR4, CCR5, CCR6 and CCR8

Given the broad agonist activities of U83A combined with the antagonist properties of the spliced truncated form U83A-Npep, there are many potential applications. Some of these have implications for pathogenesis of HHV-6 while others may be beneficial in immunotherapeutic treatments of refractive cancer proliferations or autoimmune inflammatory conditions. There are also applications as anti-microbials, clearly for HIV as discussed above, but also as a general anti-microbial agent given the similarity to properties of CCL20 and the behaviour of that chemokine and structurally related chemokines in wide spectrum anti-bacterial properties similar to beta-defensins which also interact with CCR6 like CCL20.

The applications to cancer immunotherapeutics is in three main areas including agonism of a therapeutic cellular infiltrate, antagonism of a pathogenic infiltrate and stem cell protection during cancer chemotherapy. The first area involves U83A agonism properties to chemoattract and activate cells bearing CCR1, CCR4, CCR6 and CCR8, which jointly would act to increase antigenicity and clearance of tumor cells. This also has wide applicability to action of other vaccine or DNA immunotherapeutic agents. There is evidence to date for chemokines interacting with leukocytes bearing CCR1, CCR6 and CCR8. In the case of CCR1 and CCR6 this relates to their expression on immature dendritic cells (immDC), thus chemokines which attract and activate these essential antigen presenting cells can induce the antigenicity of co-presented vaccine or DNA immunotherapeutic molecule. In the case of tumours, these often have reduced antigenicity and recent studies have shown that using existing cellular chemokines which can chemoattract CCR1 or CCR6, although not both as the case for U83A, that they can dramatically increase antigenicity, leading to increase in therapeutic infiltrates and reductions in experimental tumor models. DC play a central role in the immune response, and thus can act as cellular adjuvants in tumor vaccine therapy. In a mouse study DC precursors expressed CCR1 and CCR5, and thus were recruited to inflammatory tissue by CCL3. Injection of CCL3 mobilised DC precursors pulsed with B16 tumor lysated resulting in B16 specific immunity (54). In an A20 leukemic/lymphoma vaccine model, subcutaneous infection of CCL3 together with IL-2 or GM-CSF (but not each alone) increased survival. The results showed that CCL3 and IL-2 gave CD8 T and NK activity while best results were with CCL3 plus GM-CSF giving CD4/CD8 T cell responses, thus the T help critical for long term protection (55). In a more targeted approach, CCL16 was used which responds to both CCR1 and CCR8 expressed on and thus chemoattracting monocytes, lymphocytes and polymorphonuclear leukocytes. The chemokine gene was fused to an anti-tumor antibody light chain (TNT-3) which targets tumors by binding DNA in necrotic areas. This was then tested in a solid tumor mouse model resulting in tumor reduction which correlated with an increased infiltration of immune cells including CD4/8 T cells, PMN, B, and CD11c+CD11b+DC (56). This is a new approach to immunotherapy of solid tumors. Similar studies have also used the CCL20 chemokine to target CCR6 on bone marrow derived immature DC. Here murine tumor models of CT26 colon adenocarcinoma, and B16 melanoma were used. If CCL20 was introduced in the tumor it increased tumoral circulating DC and regression of tumors. CCL20 with CpG (not CpG alone) resulted in tumoral DC to present antigen to CD8+ cells. Thus use of DC manipulation in vivo to increase T cell mediated and tumor response (57). Similar results were found in a colorectal murine tumor model where CCL3 or CCL20 decreased tumorigenesis associated with increase CD8T cell, NK and DC. For melanomas the addition of HSVtk (not tk alone) also increased protection of a tumor challenge (58). Fusions of CCL20 with non-immune tumor antigens also showed that DNA immunizations with these fusion genes and not fusions which chemoattract mature DC (CCL21, SDF1, CXCL12) resulted in humoral protective and therapeutic immunity against two different models of sygeneic lymphomas, while use of viral chemokine fusions can overcome the hazards of inducing autoimmune reactions to host chemokines (59, 60). Thus, clearly a molecule such as U83A which combines properties of chemokines specific for CCR1, CCR6 as well as CCR8 would have combinatorial benefit in this application and could have wider implications for vaccine or immunotherapeutic use in general.

The second main area in cancer immunotherapeutics would involve antagonist properties, which would be an application for the U83A-Npep or modifications of U83A. CCR1, CCR4, CCR6 and CCR8 are either present on leukocyte infiltrates (CCR1), cutaneous T cell lymphoma or HTLV ATL (adult T cell leukaemia) (CCR4), liver metastases (CCR6) or receptors for ligands inhibiting apoptosis in ATL (CCR8) (61-65). Thus ligands that can block these receptors can inhibit the pathogenic leukocyte infiltrates. Recent studies show if novel anti-cancer strategies by inhibiting these responses. In a murine model of breast cancer Met-CCL5, an antagonist of CCR1 and CCR5, decreased the weight of tumors and infiltrating macrophages. Here the tumour was originally secreting CCL5 and the leukocyte infiltrate the CCL5 receptors CCR1 and CCR5 (Robinson 2003). Furthermore, both vMIPI and CCL1, ligands of CCR8, rescue thymic lymphoma cells from apoptosis, but addition of viral chemokine CCR8 antagonist MC148/vM-CCI inhibits this rescue activity (66).

The third possible activity for U83A is in augmenting cancer therapy. U83A has similar activities to both CCL20 and CCL3 ligands of CCR6 and CCR1 respectively. Both the human ligands also have properties in inhibiting myeloid progenitors in colony formation assays (67) and interestingly a similar property has been described for a secreted HHV-6 protein (68, 69), with enhanced effects from HHV-6A reported (70, 71). A chemokine with a similar inhibitory property is currently being developed by Human Genome Sciences as a biological for protection of bone marrow progenitor cells during cancer chemo or radiotherapy. Other recent studies show that CCL20 can also inhibit the proliferation of chronic myelogenous leukaemia progenitors, thus a direct biological for cancer therapy (72).

The other main area for applications is in autoimmune inflammatory disease, these are based on properties of CCR1, CCR4, CCR5, CCR6 and CCR8 implicated in this pathology. Data is for CNS inflammatory disease (MS, Alzheimer's), Rheumatoid Arthritis, Asthma, Diabetes, transplantation rejection, as well as some evidence for other autoimmune disorders atheriosclerosis, inflammatory bowel disease, and systemic lupus erythematosus. So here antagonist properties of versions of U83A would be of possible benefit, such as U83A-Npep or modifications of U83A itself. The most interesting area with respect to the biology of HHV-6 is in associations with CNS disease, including multiple sclerosis as well as Alzheimer's disease. CCR1 is a main target in animal models of MS, EAE, experimental autoimmune encephalitis. A CCR1 antagonist decrease clinical and histopathological disease (73, 74) and in situ hybridisation and immunohistochemistry showed CCR1 in early actively demyelinating plaques in monocyte derived macrophages (75), consistent with data from CCR1 knock out which showed reduced onset of EAE (76). While in human MS brain sections both CCR1 and CCR5 were on perivascular monocytes, with CCR1 also on parenchymal monocytic cells (77). Thus an antagonist of CCR1, such as U83A-Npep made during latent or early infection, should control CCR1 derived involvement in MS, whereas the full length U83A, made late in lytic primary or reactivated infection, may enhance disease through CCR1 or CCR5. Thus, a relationship with HHV-6A infections could be complex. Interestingly, recent data shows a relationship with MS with a subset of patients who have active (either reactivated or primary) infections with HHV-6 variant A, as reviewed (5). Moreover, also in the EAE model, upregulation of CCL20 correlates to level of clinical disease (78), as full length U83A also has similar properties to CCL20, it again could act to enhance disease during active HHV-6 infection. CCR1 or CCR1 like activity could also be involved in other inflammatory brain disease as recent results from Berlex also show that CCR1 immunoreactivity is an early marker of Alzheimer's, expressed in senile plaques with amyloid beta peptide 1-42 (79). Recent results have shown a relative increase of HHV-6 DNA in biopsies of Alzheimer's patients compared to age-matched controls (80). Overall, U83A-Npep could be used therapeutically here, while the full length U83A may be considered a target of these diseases, while the mechanism that inhibits the cellular splicing giving rise to U83A-Npep could also be considered a unique target for these diseases.

Other main areas of autoimmune inflammatory diseases to consider include rheumatoid arthritis, asthma and processes during transplantation rejection. CCR1 is being actively pursued as a target for rheumatoid arthritis (ie Chemocentryx-Forrest). A Pfizer antagonist CP-481,715 decreased 90% monocytic chemotactic activity in 11/15 rheumatoid synovial fluid samples (81) and a further proof of concept study in a phase 1b clinical trial of a CCR1 antagonist showed a decrease of macrophages and CCR1+ cells in the synovium, with a trend for clinical improvement (82).

CCR4 and CCR8 are both targets in asthmatic disease as there is an infiltration of TH2 lymphocytes in bronchial asthma, which express in particular CCR4, while CCR8 activity has also been identified in eosinophil infiltrations. There is some conflict between mouse models and human data, but concentrating on the human data show elevated CCR4 ligand in broncheoalveolar lavage (BAL) of asthmatics as well as in the bronchial epithelium of stable asthmatics (83). Studies at Roche (Milan) show CCR4 on almost all infiltrating T cells, with CCR8 on about a quarter, while ligands upregulated on airway epithelial cells upon allergen challenge (84). Further study on the role of CCR8, show inhibition with antibody to CCL1 ligand reduced eosinophil migration with no effect on allergen specific TH2 cells (85). Thus, an agent such as U83A-Npep which could target both CCR4 and CCR8 could be beneficial here.

The role of CCR4 positive TH2 cells in other autoimmune disease has also been demonstrated in a NOD mice model of diabetes where CCR4 is exclusively on memory CD4+ T cells during progression of the disease. Studies show the CCR4 chemokine ligand CCL17 on islets of prediabetic mice, with chemokine neutralisation using antibody decreasing CCR4 T cells in pancreatic infiltrates resulting in inhibition of insulitis and diabetes improvement. Whereas transgenic CCL17 NOD mice had increased CCR4 cells and an acceleration of disease (86).

Both CCR1 and CCR8 have been implicated in processes leading to transplant rejection. Met-CCL5 biological blocks CCR1 and CCR5, with treatment leading to a decrease in cardiac allograft vasculopathy in a murine model, showing both decreases in mononuclear cell recruitment and proliferative responses to donor antigen, thus CCR1 and CCR5 have roles in chronic rejection and are potential therapeutic targets. DNA transfections were undertaken to test the concept of immunomodulatory molecules into allografts by gene transfer to decrease side effects of systemic immunosuppression. Here plasmid DNA from viral chemokine antagonists vMIPII (broad), MC148 (CCR8) were transferred into the allograft at the time of transplantation. Both resulted in a decrease of donor-specific CTL infiltrating grafts and inhibited alloantibody production in cardiac allografts of mice (87). Thus providing a strategy to use antagonist biologicals, which could include U83A-Npep, as novel immunotherapeutics for alloactivation. Interestingly, it is HHV-6 reactivations which are associated with pathology leading to rejection in transplantation patients (5), here U83A full length in particular could enhance CCR1 and CCR8 activities, while the U83A-Npep could be used therapeutically, while in natural infections this would be repressed in reactivated virus during the immunosuppressive treatment of transplantation patients.

The final main area of applications for these novel biologicals are as anti-microbials. Given the similarity of U83A to properties of CCL20, it may act like betadefensins which also bind to CCR6. Both CCL20 and betadefensins have wide anti-microbial activity against a various bacterial and yeast strains (88). At least 17 other chemokines have varying antimicrobial activity, with possible similarities on their surface charge distribution. Further both defensins and selected chemokines linked to idiotypic lymphoma antigen gave potent anti-tumor vaccines (59) with acting as cellular adjuvants or possibly a direct mechanism on the tumor cell membrane. The possible anti-HIV effects are discussed above with further details on mechanisms below.

Taken together the results show that U83A and derivatives are highly efficient chemokine ligands of CCR5, showing the highest affinity interactions to date. These interactions inhibit infectivity of HIV-1 strains which use CCR5 as co-receptor, the primary receptor for HIV-1 transmission. The data shows that this is not by receptor internalisation, but that infection inhibition correlates with affinity of binding, thus there is competitive inhibition of binding. This binding also stops normal functioning of the receptor in chemotaxis stimulated by natural human chemokine ligands.

As described earlier, the difference for U83A with broad betachemokine agonist properties, from any other agent, is that it has the potential to inhibit HIV through blocking chemokine co-receptors, while at the same time acting as a cellular adjuvant to enhance immunogenicity chemoattracting cellular mediators of immunity as described above, thus a novel property combining drug-like inhibitory activity with an immunotherapeutic. Interestingly, there is some correlation with results from in vivo studies, which show that HHV-6 viral loads detected in the blood are lowered coincident with the depletion of its target cell, the CD4 T lymphocyte during HIV/AIDS progression (53, 98, 52). Thus, in the case of HHV-6A infection, this depletion in the blood may also enhance HIV replication in other cell types by removal of a natural, albeit viral, chemokine inhibitor.

In investigating entry inhibitors such as CCR5 inhibitors, an assumption is that their action stops fusion of the virion envelope with the host cell membrane to prevent release of the viral capsid into the cytosol. This can be done by competitive inhibition for binding CCR5 or from internalisation of CCR5; furthermore CCR5 binding may affect signaling. Previously described natural CCR5 antibodies and chemokine ligands appeared to affect receptor internalisation (93, 97) while selected small molecule antagonists affected receptor binding either through direct competition or allosteric effects (92, 94, 99, 100). Modification of chemokine ligands can also inhibit internalisation (101). The data shown here demonstrates that U83A unlike modified or natural chemokine ligands is not inhibiting HIV-1 infection by receptor internalisation, but rather via direct competition or allosteric effects. Thus U83A or its derivative may be an effective HIV-1 therapeutic with properties of infection inhibition and immunostimulation. It may also have utility with synergistic effects with existing HIV-1 therapies (including small molecule CCR5 inhibitors), which may prevent emergence of combination escape mutant virus.

The results demonstrate the interaction with HIV-1 by showing that U83A effectively inhibits infectivity. This is via high affinity interactions with CCR5 which block human chemokine binding as well as mediated chemotaxis and receptor internalisation. The results show CCR5 interactions in U373 derived cell lines used to assay HIV-1 infection, as well as in human ex vivo PBMC and characterise mechanism of HIV-1 inhibition demonstrating the use of U83A and UA83AN in the treatment of HIV. Thus, the results show the use of U83A and derivatives towards cellular adjuvant for vaccination to chemoattract and signal via chemokine receptors which are present on immune effector and antigen presenting cells. As demonstrated, U83A and derivatives can also act to directly inhibit HIV-1 infection. Thus presentation of HIV-1 antigens (peptide or DNA or even virus) with U83A or derivatives can act as an inhibitor and a vaccine adjuvant at the same time showing the new utility and concept of combining small molecule drug-like capacity with vaccine like properties. This can be used in immunisations, systemically or mucosally, as well as in topical microbicide preparations. Given the skin homing properties of some of the chemokine receptors which U83A can activate (CCR4, CCR8, CCR6) as well as inducible inflammatory receptors (CCR1 and CCR5), U83A may also have particular utility in skin mucosal directed vaccinations.

So, in summary both the activities of U83A or U83A-Npep could have a variety of activities in applications from three main areas including cancer as vaccine or immunotherapeutics, autoimmune disease as antagonist, and antimicrobial as antagonist or agonist in derived vaccines or immunotherapeutics. Thus, the unique cellular reactivity of the full length U83A combined with the opposing activity of the spliced U83A-Npep form a potent arsenal which appear to direct crucial functions during the virus life cycle inhibiting immune surveillance prior to replication then chemoattracting selected cells for virus dissemination during active lytic replication. These unique combinatorial properties could target at least a proportion of the estimated US$13 billion immunotherapeutic market (D&MD publications).

REFERENCES

1. Dominguez, G., T. R. Dambaugh, F. R. Stamey, S. Dewhurst, N. Inoue, and P. E. Pellett. 1999. Human herpesvirus 6B genome sequence: coding content and comparison with human herpesvirus 6A. *J Virol* 73:8040.
2. Gompels, U. A., J. Nicholas, G. Lawrence, M. Jones, B. J. Thomson, M. E. Martin, S. Efstathiou, M. Craxton, and H. A. Macaulay. 1995. The DNA sequence of human herpesvirus-6: structure, coding content, and genome evolution. *Virology* 209:29.
3. Isegawa, Y., T. Mukai, K. Nakano, M. Kagawa, J. Chen, Y. Mori, T. Sunagawa, K. Kawanishi, J. Sashihara, A. Hata, P. Zou, H. Kosuge, and K. Yamanishi. 1999. Comparison of the complete DNA sequences of human herpesvirus 6 variants A and B. *J Virol* 73:8053.
4. Kasolo, F. C., E. Mpabalwani, and U. A. Gompels. 1997. Infection with AIDS-related herpesviruses in human immunodeficiency virus-negative infants and endemic childhood Kaposi's sarcoma in Africa. *J Gen Virol* 78 (Pt 4):847.
5. Gompels, U. A. 2004. Roseoloviruses: human herpesviruses 6 and 7. In *Principles and practice of Clinical Virology Fifth Edition*. A. J. Zuckerman, J. E. Banatvala, J. R. Pattison, P. D. Griffiths, and B. D. Schoub, eds. John Wiley & Sons Ltd, Chichester, p. 147.
6. Akhyani, N., R. Berti, M. B. Brennan, S. S. Soldan, J. M. Eaton, H. F. McFarland, and S. Jacobson. 2000. Tissue distribution and variant characterization of human herpesvirus (HHV)-6: increased prevalence of HHV-6A in patients with multiple sclerosis. *J Infect Dis* 182:1321.
7. Soldan, S. S., T. P. Leist, K. N. Juhng, H. F. McFarland, and S. Jacobson. 2000. Increased lymphoproliferative response to human herpesvirus type 6A variant in multiple sclerosis patients. *Ann Neurol* 47:306.
8. Kim, J. S., K. S. Lee, J. H. Park, M. Y. Kim, and W. S. Shin. 2000. Detection of human herpesvirus 6 variant A in peripheral blood mononuclear cells from multiple sclerosis patients. *Eur Neurol* 43:170.
9. Alvarez-Lafuente, R., V. De las Heras, M. Bartolome, J. J. Picazo, and R. Arroyo. 2004. Relapsing-remitting multiple sclerosis and human herpesvirus 6 active infection. *Arch Neurol* 61:1523.
10. Rotola, A., E. Merlotti, L. Caniatti, E. Caselli, E. Granieri, M. R. Tola, D. Di Luca, and E. Cassai. 2004. Human herpesvirus 6 infects the central nervous system of multiple sclerosis patients in the early stages of the disease. *Mult Scler* 10:348.
11. Akter, P., C. Cunningham, B. P. McSharry, A. Dolan, C. Addison, D. J. Dugan, A. F. Hassan-Walker, V. C. Emery, P. D. Griffiths, G. W. Wilkinson, and A. J. Davison. 2003. Two novel spliced genes in human cytomegalovirus. *J Gen Virol* 84:1117.
12. Gerna, G., E. Percivalle, D. Lilleri, L. Lozza, C. Fornara, G. Hahn, F. Baldanti, and M. G. Revello. 2005. Dendritic-cell infection by human cytomegalovirus is restricted to strains carrying functional UL131-128 genes and mediates efficient viral antigen presentation to CD8+ T cells. *J Gen Virol* 86:275.
13. Hahn, G., M. G. Revello, M. Patrone, E. Percivalle, G. Campanini, A. Sarasini, M. Wagner, A. Gallina, G. Milanesi, U. Koszinowski, F. Baldanti, and G. Gerna. 2004. Human cytomegalovirus UL131-128 genes are indispensable for virus growth in endothelial cells and virus transfer to leukocytes. *J Virol* 78:10023.
14. Saederup, N., S. A. Aguirre, T. E. Sparer, D. M. Bouley, and E. S. Mocarski. 2001. Murine cytomegalovirus CC chemokine homolog MCK-2 (m131-129) is a determinant of dissemination that increases inflammation at initial sites of infection. *J Virol* 75: 9966.
15. Saederup, N., Y. C. Lin, D. J. Dairaghi, T. J. Schall, and E. S. Mocarski. 1999. Cytomegalovirus-encoded beta chemokine promotes monocyte-associated viremia in the host. *Proc Natl Acad Sci USA* 96:10881.
16. Fleming, P., N. Davis-Poynter, M. Degli-Esposti, E. Densley, J. Papadimitriou, G. Shellam, and H. Farrell. 1999. The murine cytomegalovirus chemokine homolog, m131/129, is a determinant of viral pathogenicity. *J Virol* 73:6800.
17. Luttichau, H. R., I. Clark-Lewis, P. O. Jensen, C. Moser, J. Gerstoft, and T. W. Schwartz. 2003. A highly selective CCR2 chemokine agonist encoded by human herpesvirus 6. *J Biol Chem* 278:10928.
18. Zou, P., Y. Isegawa, K. Nakano, M. Hague, Y. Horiguchi, and K. Yamanishi. 1999. Human herpesvirus 6 open reading frame U83 encodes a functional chemokine. *J Virol* 73:5926.
19. Smith, D., and K. S. Johnson. 1988. Single-step purification of polypeptides expressed in Escherichia coli as fusions with glutatione S-transferase. *Gene* 67:31.
20. Bradford, M. M. 1976. A rapid and sensitive method for the quantitation of microgram quantities of protein utilizing the principle of protein-dye binding. *Anal. Biochem.* 72:248.
21. Proudfoot, A. E., and F. Borlat. 2000. Analysis, quantitation and storage of chemokines. *Methods in Molecular Biology* 138:85.
22. Tsuchiya, S., M. Yamabe, Y. Yamaguchi, Y. Kobayashi, T. Kono, and K. Tada. 1980. Establishment and characterisation of a human acute monocytic leukaemia cell line (THP-1). *International J. Cancer* 26:171.
23. Klein, E. 1976. Properties of the K562 cell line, derived from a patient with chronic myeloid leukaemia. *International J. Cancer* 18:421.
24. Gazdar, A. F., D. N. Carney, P. A. Bunn, E. K. Russell, E. S. Jaffe, G. P. Schechter, and J. G. Guccion. 1980. Mitogen requirements for the in vitro propagation of cutaneous T-cell lymphomas. *Blood* 55:409.
25. Milne, R. S., C. Mattick, L. Nicholson, P. Devaraj, A. Alcami, and U. A. Gompels. 2000. RANTES binding and down-regulation by a novel human herpesvirus-6 beta chemokine receptor. *J Immunol* 164:2396.
26. French, C., P. Menegazzi, L. Nicholson, H. Macaulay, D. DiLuca, and U. A. Gompels. 1999. Novel, nonconsensus cellular splicing regulates expression of a gene encoding a chemokine-like protein that shows high variation and is specific for human herpesvirus 6. *Virology* 262:139.
27. Kledal, T. N., M. M. Rosenkilde, F. Coulin, G. Simmons, A. H. Johnsen, S. Alouani, C. A. Power, H. R. Luttichau, J. Gerstoft, P. R. Clapham, I. Clark-Lewis, T. N. Wells, and T. W. Schwartz. 1997. A broad-spectrum chemokine antagonist encoded by Kaposi's sarcoma-associated herpesvirus. *Science* 277:1656.
28. Boshoff, C., Y. Endo, P. D. Collins, Y. Takeuchi, J. D. Reeves, V. L. Schweickart, M. A. Siani, T. Sasaki, T. J. Williams, P. W. Gray, P. S. Moore, Y. Chang, and R. A. Weiss. 1997. Angiogenic and HIV-inhibitory functions of KSHV-encoded chemokines. *Science* 278:290.
29. Pal, R., A. Garzino-Demo, P. D. Markham, J. Burns, M. Brown, R. C. Gallo, and A. L. DeVico. 1997 Inhibition of HIV-1 infection by the beta-chemokine MDC. *Science* 278: 695.
30. Struyf, S., P. Proost, S. Sozzani, A. Mantovani, A. Wuyts, E. De Clercq, D. Schols, and J. Van Damme. 1998.

Enhanced anti-HIV-1 activity and altered chemotactic potency of NH2-terminally processed macrophage-derived chemokine (MDC) imply an additional MDC receptor. *J Immunol* 161:2672.
31. Utaipat, U., A. Duerr, D. L. Rudolph, C. Yang, S. T. Butera, D. Lupo, T. Pisell, A. Tangmunkongvorakul, N. Kamtorn, N. Nantachit, T. Nagachinta, V. Suriyanon, V. Robison, K. E. Nelson, N. Sittisombut, and R. B. Lal. 2002. Coreceptor utilization of HIV type 1 subtype E viral isolates from Thai men with HIV type 1-infected and uninfected wives. *AIDS Res Hum Retroviruses* 18:1.
32. Lee, S., H. L. Tiffany, L. King, P. M. Murphy, H. Golding, and M. B. Zaitseva. 2000. CCR8 on human thymocytes functions as a human immunodeficiency virus type 1 coreceptor. *J Virol* 74:6946.
33. Spenlehauer, C., C. A. Gordon, A. Trkola, and J. P. Moore. 2001. A luciferase-reporter gene-expressing T-cell line facilitates neutralization and drug-sensitivity assays that use either R5 or X4 strains of human immunodeficiency virus type 1. *Virology* 280: 292.
34. Dejucq, N., G. Simmons, and P. R. Clapham. 1999. Expanded tropism of primary human immunodeficiency virus type 1 R5 strains to CD4(+) T-cell lines determined by the capacity to exploit low concentrations of CCR5. *J Virol* 73:7842.
35. Di Luca, D., P. Mirandola, T. Ravaioli, B. Bigoni, and E. Cassai. 1996. Distribution of HHV-6 variants in human tissues. *Infect Agents Dis* 5:203.
36. Nicholas, J. 1996. Determination and analysis of the complete nucleotide sequence of human herpesvirus. *J Virol* 70:5975.
37. Luttichau, H. R., J. Gerstoft, and T. W. Schwartz. 2001. MC148 encoded by human molluscum contagiosum poxvirus is an antagonist for human but not murine CCR8. *J Leukoc Biol* 70:277.
38. Endres, M. J., C. G. Garlisi, H. Xiao, L. Shan, and J. A. Hedrick. 1999. The Kaposi's sarcoma-related herpesvirus (KSHV)-encoded chemokine vMIP-I is a specific agonist for the CC chemokine receptor (CCR)8. *J Exp Med* 189:1993.
39. Dairaghi, D. J., R. A. Fan, B. E. McMaster, M. R. Hanley, and T. J. Schall. 1999. HHV8-encoded vMIP-I selectively engages chemokine receptor CCR8. Agonist and antagonist profiles of viral chemokines. *J Biol Chem* 274:21569.
40. Luttichau, H. R., I. C. Lewis, J. Gerstoft, and T. W. Schwartz. 2001. The herpesvirus 8-encoded chemokine vMIP-II, but not the poxvirus-encoded chemokine MC148, inhibits the CCR10 receptor. *Eur J Immunol* 31:1217.
41. Sozzani, S., W. Luini, G. Bianchi, P. Allavena, T. N. Wells, M. Napolitano, G. Bernardini, A. Vecchi, D. D'Ambrosio, D. Mazzeo, F. Sinigaglia, A. Santoni, E. Maggi, S. Romagnani, and A. Mantovani. 1998. The viral chemokine macrophage inflammatory protein-II is a selective Th2 chemoattractant. *Blood* 92:4036.
42. Stine, J. T., C. Wood, M. Hill, A. Epp, C. J. Raport, V. L. Schweickart, Y. Endo, T. Sasaki, G. Simmons, C. Boshoff, P. Clapham, Y. Chang, P. Moore, P. W. Gray, and D. Chantry. 2000. KSHV-encoded CC chemokine vMIP-III is a CCR4 agonist, stimulates angiogenesis, and selectively chemoattracts TH2 cells. *Blood* 95:1151.
43. Penfold, M. E., D. J. Dairaghi, G. M. Duke, N. Saederup, E. S. Mocarski, G. W. Kemble, and T. J. Schall. 1999. Cytomegalovirus encodes a potent alpha chemokine. *Proc Natl Acad Sci USA* 96:9839.
44. Damon, I., P. M. Murphy, and B. Moss. 1998. Broad spectrum chemokine antagonistic activity of a human poxvirus chemokine homolog. *Proc Natl Acad Sci USA* 95:6403.
45. Luttichau, H. R., J. Stine, T. P. Boesen, A. H. Johnsen, D. Chantry, J. Gerstoft, and T. W. Schwartz. 2000. A highly selective CC chemokine receptor (CCR)8 antagonist encoded by the poxvirus molluscum contagiosum. *J Exp Med* 191:171.
46. Penfold, M., Z. Miao, Y. Wang, S. Haggerty, and M. R. Schleiss. 2003. A macrophage inflammatory protein homolog encoded by guinea pig cytomegalovirus signals via CC chemokine receptor 1. *Virology* 316:202.
47. Agrawal, L., Z. Vanhorn-Ali, and G. Alkhatib. 2002. Multiple determinants are involved in HIV coreceptor use as demonstrated by CCR4/CCL22 interaction in peripheral blood mononuclear cells (PBMCs). *J Leukoc Biol* 72:1063.
48. Clapham, P. R., and A. McKnight. 2001. HIV-1 receptors and cell tropism. *Br Med Bull* 58:43.
49. Clapham, P. R., and A. McKnight. 2002. Cell surface receptors, virus entry and tropism of primate lentiviruses. *J Gen Virol* 83:1809.
50. Emery, V. C., M. C. Atkins, E. F. Bowen, D. A. Clark, M. A. Johnson, I. M. Kidd, J. E. McLaughlin, A. N. Phillips, P. M. Strappe, and P. D. Griffiths. 1999. Interactions between beta-herpesviruses and human immunodeficiency virus in vivo: evidence for increased human immunodeficiency viral load in the presence of human herpesvirus 6. *J Med Virol* 57:278.
51. Fairfax, M. R., T. Schacker, R. W. Cone, A. C. Collier, and L. Corey. 1994. Human herpesvirus 6 DNA in blood cells of human immunodeficiency virus-infected men: correlation of high levels with high CD4 cell counts. *J Infect Dis* 169:1342.
52. Knox, K. K., and D. R. Carrigan. 1994. Disseminated active HHV-6 infections in patients with AIDS. *Lancet* 343:577.
53. Corbellino, M., P. Lusso, R. C. Gallo, C. Parravicini, M. Galli, and M. Moroni. 1993. Disseminated human herpesvirus 6 infection in AIDS. *Lancet* 342:1242.
54. Zhang, Y., H. Yoneyama, Y. Wang, S. Ishikawa, S. Hashimoto, J. L. Gao, P. Murphy, and K. Matsushima. 2004. Mobilization of dendritic cell precursors into the circulation by administration of MIP-1 alpha in mice. *J Natl Cancer Inst* 96:201.
55. Zibert, A., S. Balzer, M. Souquet, T. H. Quang, C. Paris-Scholz, M. Roskrow, and D. Dilloo. 2004. CCL3/MIP-1 alpha is a potent immunostimulator when coexpressed with interleukin-2 or granulocyte-macrophage colony-stimulating factor in a leukemia/lymphoma vaccine. *Hum Gene Ther* 15:21.
56. Li, J., P. Hu, L. A. Khawli, and A. L. Epstein. 2003. Complete regression of experimental solid tumors by combination LEC/chTNT-3 immunotherapy and CD25(+) T-cell depletion. *Cancer Res* 63: 8384.
57. Furumoto, K., L. Soares, E. G. Engleman, and M. Merad. 2004. Induction of potent antitumor immunity by in situ targeting of intratumoral DCs. *J Clin Invest* 113: 774.
58. Crittenden, M., M. Gough, K. Harrington, K. Olivier, J. Thompson, and R. G. Vile. 2003. Expression of inflammatory chemokines combined with local tumor destruction enhances tumor regression and long-term immunity. *Cancer Res* 63:5505.
59. Biragyn, A., M. Surenhu, D. Yang, P. A. Ruffini, B. A. Haines, E. Klyushnenkova, J. J. Oppenheim, and L. W.

Kwak. 2001. Mediators of innate immunity that target immature, but not mature, dendritic cells induce antitumor immunity when genetically fused with nonimmunogenic tumor antigens. *J Immunol* 167:6644.
60. Biragyn, A., P. A. Ruffini, M. Coscia, L. K. Harvey, S. S. Neelapu, S. Baskar, J. M. Wang, and L. W. Kwak. 2004. Chemokine receptor-mediated delivery directs self-tumor antigen efficiently into the class II processing pathway in vitro and induces protective immunity in vivo. *Blood* 104:1961.
61. Yoshie, O., R. Fujisawa, T. Nakayama, H. Harasawa, H. Tago, D. Izawa, K. Hieshima, Y. Tatsumi, K. Matsushima, H. Hasegawa, A. Kanamaru, S. Kamihira, and Y. Yamada. 2002. Frequent expression of CCR4 in adult T-cell leukemia and human T-cell leukemia virus type 1-transformed T cells. *Blood* 99:1505.
62. Ruckes, T., D. Saul, J. Van Snick, O. Hermine, and R. Grassmann. 2001. Autocrine antiapoptotic stimulation of cultured adult T-cell leukemia cells by overexpression of the chemokine 1-309. *Blood* 98:1150.
63. Robinson, S. C., K. A. Scott, J. L. Wilson, R. G. Thompson, A. E. Proudfoot, and F. R. Balkwill. 2003. A chemokine receptor antagonist inhibits experimental breast tumor growth. *Cancer Res* 63:8360.
64. Ferenczi, K., R. C. Fuhlbrigge, J. Pinkus, G. S. Pinkus, and T. S. Kupper. 2002. Increased CCR4 expression in cutaneous T cell lymphoma. *J Invest Dermatol* 119:1405.
65. Dellacasagrande, J., O. J. Schreurs, P. O. Hofgaard, H. Omholt, S. Steinsvoll, K. Schenck, B. Bogen, and Z. Dembic. 2003. Liver metastasis of cancer facilitated by chemokine receptor CCR6. *Scand J Immunol* 57:534.
66. Spinetti, G., G. Bernardini, G. Camarda, A. Mangoni, A. Santoni, M. C. Capogrossi, and M. Napolitano. 2003. The chemokine receptor CCR8 mediates rescue from dexamethasone-induced apoptosis via an ERK-dependent pathway. *J Leukoc Biol* 73:201.
67. Broxmeyer, H. E., C. H. Kim, S. H. Cooper, G. Hangoc, R. Hromas, and L. M. Pelus. 1999. Effects of CC, CXC, C, and CX3C chemokines on proliferation of myeloid progenitor cells, and insights into SDF-1-induced chemotaxis of progenitors. *Ann N Y Acad Sci* 872:142.
68. Isomura, H., M. Yamada, M. Yoshida, H. Tanaka, T. Kitamura, M. Oda, S. Nii, and Y. Seino. 1997. Suppressive effects of human herpesvirus 6 on in vitro colony formation of hematopoietic progenitor cells. *J Med Virol* 52:406.
69. Knox, K. K., and D. R. Carrigan. 1992. In vitro suppression of bone marrow progenitor cell differentiation by human herpesvirus 6 infection. *J Infect Dis* 165:925.
70. Carrigan, D. R., and K. K. Knox. 1995. Bone marrow suppression by human herpesvirus-6: comparison of the A and B variants of the virus. *Blood* 86:835.
71. Nitsche, A., J. Fleischmann, K. M. Klima, A. Radonic, S. Thulke, and W. Siegert. 2004 Inhibition of cord blood cell expansion by human herpesvirus 6 in vitro. *Stem Cells Dev* 13:197.
72. Hromas, R., L. Cripe, G. Hangoc, S. Cooper, and H. E. Broxmeyer. 2000. The exodus subfamily of CC chemokines inhibits the proliferation of chronic myelogenous leukemia progenitors. *Blood* 95:1506.
73. Eltayeb, S., D. Sunnemark, A. L. Berg, G. Nordvall, A. Malmberg, H. Lassmann, E. Wallstrom, T. Olsson, and A. Ericsson-Dahlstrand. 2003. Effector stage CC chemokine receptor-1 selective antagonism reduces multiple sclerosis-like rat disease. *J Neuroimmunol* 142:75.
74. Liang, M., C. Mallari, M. Rosser, H. P. Ng, K. May, S. Monahan, J. G. Bauman, I. Islam, A. Ghannam, B. Buckman, K. Shaw, G. P. Wei, W. Xu, Z. Zhao, E. Ho, J. Shen, H. Oanh, B. Subramanyam, R. Vergona, D. Taub, L. Dunning, S. Harvey, R. M. Snider, J. Hesselgesser, M. M. Morrissey, and H. D. Perez. 2000. Identification and characterization of a potent, selective, and orally active antagonist of the CC chemokine receptor-1. *J Biol Chem* 275:19000.
75. Sunnemark, D., S. Eltayeb, E. Wallstrom, L. Appelsved, A. Malmberg, H. Lassmann, A. Ericsson-Dahlstrand, F. Piehl, and T. Olsson. 2003. Differential expression of the chemokine receptors CX3CR1 and CCR1 by microglia and macrophages in myelin-oligodendrocyte-glycoprotein-induced experimental autoimmune encephalomyelitis. *Brain Pathol* 13:617.
76. Rottman, J. B., A. J. Slavin, R. Silva, H. L. Weiner, C. G. Gerard, and W. W. Hancock. 2000. Leukocyte recruitment during onset of experimental allergic encephalomyelitis is CCR1 dependent. *Eur J Immunol* 30:2372.
77. Trebst, C., S. M. Staugaitis, B. Tucky, T. Wei, K. Suzuki, K. D. Aldape, C. A. Pardo, J. Troncoso, H. Lassmann, and R. M. Ransohoff. 2003. Chemokine receptors on infiltrating leucocytes in inflammatory pathologies of the central nervous system (CNS). *Neuropathol Appl Neurobiol* 29:584.
78. Kohler, R. E., A. C. Caon, D. O. Willenborg, I. Clark-Lewis, and S. R. McColl. 2003. A role for macrophage inflammatory protein-3 alpha/CC chemokine ligand 20 in immune priming during T cell-mediated inflammation of the central nervous system. *J Immunol* 170:6298.
79. Halks-Miller, M., M. L. Schroeder, V. Haroutunian, U. Moenning, M. Rossi, C. Achim, D. Purohit, M. Mahmoudi, and R. Horuk. 2003. CCR1 is an early and specific marker of Alzheimer's disease. *Ann Neurol* 54:638.
80. Lin, W. R., M. A. Wozniak, R. J. Cooper, G. K. Wilcock, and R. F. Itzhaki. 2002. Herpesviruses in brain and Alzheimer's disease. *J Pathol* 197:395.
81. Gladue, R. P., L. A. Tylaska, W. H. Brissette, P. D. Lira, J. C. Kath, C. S. Poss, M. F. Brown, T. J. Paradis, M. J. Conklyn, K. T. Ogborne, M. A. McGlynn, B. M. Lillie, A. P. DiRico, E. N. Mairs, E. B. McElroy, W. H. Martin, I. A. Stock, R. M. Shepard, H. J. Showell, and K. Neote. 2003. CP-481,715, a potent and selective CCR1 antagonist with potential therapeutic implications for inflammatory diseases. *J Biol Chem* 278:40473.
82. Haringman, J. J., M. C. Kraan, T. J. Smeets, K. H. Zwinderman, and P. P. Tak. 2003. Chemokine blockade and chronic inflammatory disease: proof of concept in patients with rheumatoid arthritis. *Ann Rheum Dis* 62:715.
83. Lezcano-Meza, D., M. C. Negrete-Garcia, M. Dante-Escobedo, and L. M. Teran. 2003. The monocyte-derived chemokine is released in the bronchoalveolar lavage fluid of steady-state asthmatics. *Allergy* 58:1125.
84. Panina-Bordignon, P., A. Papi, M. Mariani, P. Di Lucia, G. Casoni, C. Bellettato, C. Buonsanti, D. Miotto, C. Mapp, A. Villa, G. Arrigoni, L. M. Fabbri, and F. Sinigaglia. 2001. The C-C chemokine receptors CCR4 and CCR8 identify airway T cells of allergen-challenged atopic asthmatics. *J Clin Invest* 107:1357.
85. Bishop, B., and C. M. Lloyd. 2003. CC chemokine ligand 1 promotes recruitment of eosinophils but not Th2 cells during the development of allergic airways disease. *J Immunol* 170:4810.
86. Kim, S. H., M. M. Cleary, H. S. Fox, D. Chantry, and N. Sarvetnick. 2002. CCR4-bearing T cells participate in autoimmune diabetes. *J Clin Invest* 110:1675.

87. DeBruyne, L. A., K. Li, D. K. Bishop, and J. S. Bromberg. 2000. Gene transfer of virally encoded chemokine antagonists vMIP-II and MC148 prolongs cardiac allograft survival and inhibits donor-specific immunity. *Gene Ther* 7:575.
88. Yang, D., Q. Chen, D. M. Hoover, P. Staley, K. D. Tucker, J. Lubkowski, and J. J. Oppenheim. 2003. Many chemokines including CCL20/MIP-3alpha display antimicrobial activity. *J Leukoc Biol* 74:448.
89. Dewin, D. R., J. Catusse, and U. A. Gompels. 2006. Identification and characterization of U83A viral chemokine, a broad and potent beta-chemokine agonist for human CCRs with unique selectivity and inhibition by spliced isoform. *J Immunol* 176:544-556.
90. Kledal, T. N., M. M. Rosenkilde, F. Coulin, G. Simmons, A. H. Johnsen, S. Alouani, C. A. Power, H. R. Luttichau, J. Gerstoft, P. R. Clapham, I. Clark-Lewis, T. N. Wells, and T. W. Schwartz. 1997. A broad-spectrum chemokine antagonist encoded by Kaposi's sarcoma-associated herpesvirus. *Science* 277:1656-1659.
91. Margolis, L., and R. Shattock. 2006. Selective transmission of CCR5-utilizing HIV-1: the 'gatekeeper' problem resolved? *Nat Rev Microbiol* 4:312-317.
92. Westby, M., and E. van der Ryst. 2005. CCR5 antagonists: host-targeted antivirals for the treatment of HIV infection. *Antivir Chem Chemother* 16:339-354.
93. Pastori, C., B. Weiser, C. Barassi, C. Uberti-Foppa, S. Ghezzi, R. Longhi, G. Calori, H. Burger, K. Kemal, G. Poli, A. Lazzarin, and L. Lopalco. 2006. Long lasting CCR5 internalization by antibodies in a subset of Long Term Non Progressors: a possible protective effect against disease progression. *Blood*
94. Willey, S., P. J. Peters, W. M. Sullivan, P. Dorr, M. Perros, and P. R. Clapham. 2005 Inhibition of CCR5-mediated infection by diverse R5 and R5X4 HIV and SIV isolates using novel small molecule inhibitors of CCR5: effects of viral diversity, target cell and receptor density. *Antiviral Res* 68:96-108.
95. Vodicka, M. A., W. C. Goh, L. I. Wu, M. E. Rogel, S. R. Bartz, V. L. Schweickart, C. J. Raport, and M. Emerman. 1997. Indicator cell lines for detection of primary strains of human and simian immunodeficiency viruses. *Virology* 233:193-198.
96. Cronshaw, D. G., C. Owen, Z. Brown, and S. G. Ward. 2004. Activation of phosphoinositide 3-kinases by the CCR4 ligand macrophage-derived chemokine is a dispensable signal for T lymphocyte chemotaxis. *J Immunol* 172:7761-7770.
97. Signoret, N., L. Hewlett, S. Wavre, A. Pelchen-Matthews, M. Oppermann, and M. Marsh. 2005. Agonist-induced endocytosis of CC chemokine receptor 5 is clathrin dependent. *Mol Biol Cell* 16:902-917.
98. Fairfax, M. R., T. Schacker, R. W. Cone, A. C. Collier, and L. Corey. 1994. Human herpesvirus 6 DNA in blood cells of human immunodeficiency virus-infected men: correlation of high levels with high CD4 cell counts. *J Infect Dis* 169:1342-1345.
99. Dorr, P., M. Westby, S. Dobbs, P. Griffin, B. Irvine, M. Macartney, J. Mori, G. Rickett, C. Smith-Burchnell, C. Napier, R. Webster, D. Armour, D. Price, B. Stammen, A. Wood, and M. Perms. 2005. Maraviroc (UK-427,857), a potent, orally bioavailable, and selective small-molecule inhibitor of chemokine receptor CCR5 with broad-spectrum anti-human immunodeficiency virus type 1 activity. *Antimicrob Agents Chemother* 49:4721-4732.
100. Maeda, K., D. Das, H. Ogata-Aoki, H. Nakata, T. Miyakawa, Y. Tojo, R. Norman, Y. Takaoka, J. Ding, E. Arnold, and H. Mitsuya. 2006. Structural and molecular interactions of CCR5 inhibitors with CCR5. *J Biol Chem*
101. Wells, T. N., C. A. Power, J. P. Shaw, and A. E. Proudfoot. 2006. Chemokine blockers—therapeutics in the making? *Trends Pharmacol Sci* 27:41-47.

The invention claimed is:

1. An expression vector comprising:
   (a) a polynucleotide encoding the polypeptide of SEQ ID NO:5 or SEQ ID NO:6;
   (b) a polynucleotide complementary to the polynucleotide of (a);
   (c) a polynucleotide that hybridizes to the poly nuoleotide of (b) and encodes a polypeptide that functions as an agonist of at least one cytokine receptor, wherein the at least one cytokine receptor is a cytokine receptor that is activated by the polypeptide of SEQ ID NO:5 or SEQ ID NO:6; or
   (d) a polynucleotide that hybridizes to the complement of a polynucleotide encoding the polypeptide of SEQ ID NO:7 or SEQ ID NO:8 and encodes a polypeptide that functions as an antagonist of at least one cytokine receptor, wherein the at least one cytokine receptor is a cytokine receptor that is inhibited by the polypeptide of SEQ ID NO:7 or SEQ ID NO:8, wherein hybridization occurs at 65° C. and the polynucleotides remain hybridized after washing with 0.2×SSC.

2. The expression vector of claim 1, wherein the expression vector is a eukaryotic vector.

3. The expression vector of claim 1, wherein the expression vector is a non-eukaryotic vector.

4. The expression vector of claim 1, wherein the expression vector is a bacterial, yeast, or viral vector.

5. The expression vector of claim 1, wherein the expression vector is a plasmid, a cosmid, or an artificial chromosome.

6. The expression vector of claim 1, wherein the polynucleotide encoding the polypeptide of SEQ ID NO:5 is SEQ ID NO:1; the polynucleotide encoding the polypeptide of SEQ ID NO:6 is SEQ ID NO:2; the polynucleotide encoding the polypeptide of SEQ ID NO:7 consists of SEQ ID NO:3; and the polynucleotide encoding the polypeptide of SEQ ID NO:8 is SEQ ID NO:4.

7. An isolated host cell comprising the expression vector of claim 1.

8. The host cell of claim 7, wherein the cell is eukaryotic.

9. The host cell of claim 7, wherein the cell is prokaryotic.

10. The host cell of claim 7, wherein the cell is a mammalian cell, an insect cell, a plant cell, or a bacterial cell.

11. The expression vector of claim 1, comprising:
    (a) the polynucleotide encoding the polypeptide of SEQ ID NO:5 or SEQ ID NO:6; or
    (b) the polynucleotide complementary to the polynucleotide of (a).

12. The expression vector of claim 1, wherein the polynucleotide encoding the polypeptide of SEQ ID NO:5 or SEQ ID NO:6 encodes a functional chemokine.

13. The expression vector of claim 1, wherein the expression vector comprises a polynucleotide encoding the polypeptide of SEQ ID NO:5.

14. The expression vector of claim 1, wherein the polynucleotide of part (a), part (b) or part (c) is the same length as SEQ ID NO:1 or SEQ ID NO:2, and the polynucleotide of part (d) is the same length as SEQ ID NO:3 or SEQ ID NO:4.

15. The expression vector of claim 1, wherein the expression vector is not of virus sequence origin.

* * * * *

SEQUENCE LISTING

```
<160> NUMBER OF SEQ ID NOS: 16

<210> SEQ ID NO 1
<211> LENGTH: 339
<212> TYPE: DNA
<213> ORGANISM: Human herpesvirus 6A

<400> SEQUENCE: 1
atgtccattc ggcttttat tggttttttt tatacggcat atattggtat ggctatcgga      60
tttatatgta gttcccccga tgcggagctg ttttccgaaa aatcacgtat gtcgtcttct    120
gtcttgttag gatgtttgtt gtgttgcatg gattggtccg ctgccgtacc tgggaaaaca    180 gagccttta gaaaactttt tgatgcaatc atgattaaaa agctaaaaag ttgttctgct    240
gcttacccgt ctgatttgga gcagggctcg atgtgtgata tggcagatgc atcgccgaca    300
agtcttgaat taggattgtc gaaattagac aaagaatca                          339

<210> SEQ ID NO 2
<211> LENGTH: 279
<212> TYPE: DNA
<213> ORGANISM: Human herpesvirus 6A

<400> SEQUENCE: 2
tttatatgta gttcccccga tgcggagctg ttttccgaaa aatcacgtat gtcgtcttct     60
gtcttgttag gatgtttgtt gtgttgcatg gattggtccg ctgccgtacc tgggaaaaca   120
```

```
gagccttta gaaaactttt tgatgcaatc atgattaaaa agctaaaaag ttgttctgct      180
gcttacccgt ctgatttgga gcagggctcg atgtgtgata tggcagatgc atcgccgaca      240
agtcttgaat taggattgtc gaaattagac aaagaatca                             279
```

<210> SEQ ID NO 3
<211> LENGTH: 177
<212> TYPE: DNA
<213> ORGANISM: Human herpesvirus 6A

<400> SEQUENCE: 3

```
atgtccattc ggcttttat tggtttttt tatacggcat atattggtat ggctatcgga       60
tttatatgta gttcccccga tgcggagctg ttttccgaaa aatcacgtat gtcgtcttct      120
gtcttgttag atgtttgtt gtgttgcatg gattggtccg ctgccgtacc cgtctga         177
```

<210> SEQ ID NO 4
<211> LENGTH: 117
<212> TYPE: DNA
<213> ORGANISM: Human herpesvirus 6A

<400> SEQUENCE: 4

```
tttatatgta gttcccccga tgcggagctg ttttccgaaa aatcacgtat gtcgtcttct      60
gtcttgttag atgtttgtt gtgttgcatg gattggtccg ctgccgtacc cgtctga         117
```

<210> SEQ ID NO 5
<211> LENGTH: 113
<212> TYPE: PRT
<213> ORGANISM: Human herpesvirus 6A

<400> SEQUENCE: 5

```
Met Ser Ile Arg Leu Phe Ile Gly Phe Phe Tyr Thr Ala Tyr Ile Gly
1               5                   10                  15

Met Ala Ile Gly Phe Ile Cys Ser Ser Pro Asp Ala Glu Leu Phe Ser
            20                  25                  30

Glu Lys Ser Arg Met Ser Ser Ser Val Leu Leu Gly Cys Leu Leu Cys
        35                  40                  45

Cys Met Asp Trp Ser Ala Ala Val Pro Gly Lys Thr Glu Pro Phe Arg
    50                  55                  60

Lys Leu Phe Asp Ala Ile Met Ile Lys Lys Leu Lys Ser Cys Ser Ala
65                  70                  75                  80

Ala Tyr Pro Ser Asp Leu Glu Gln Gly Ser Met Cys Asp Met Ala Asp
                85                  90                  95

Ala Ser Pro Thr Ser Leu Glu Leu Gly Leu Ser Lys Leu Asp Lys Glu
            100                 105                 110

Ser
```

<210> SEQ ID NO 6
<211> LENGTH: 93
<212> TYPE: PRT
<213> ORGANISM: Human herpesvirus 6A

<400> SEQUENCE: 6

```
Phe Ile Cys Ser Ser Pro Asp Ala Glu Leu Phe Ser Glu Lys Ser Arg
1               5                   10                  15

Met Ser Ser Ser Val Leu Leu Gly Cys Leu Leu Cys Cys Met Asp Trp
            20                  25                  30

Ser Ala Ala Val Pro Gly Lys Thr Glu Pro Phe Arg Lys Leu Phe Asp
```

```
            35                  40                  45
Ala Ile Met Ile Lys Lys Leu Lys Ser Cys Ser Ala Ala Tyr Pro Ser
    50                  55                  60

Asp Leu Glu Gln Gly Ser Met Cys Asp Met Asp Ala Ser Pro Thr
65                  70                  75                  80

Ser Leu Glu Leu Gly Leu Ser Lys Leu Asp Lys Glu Ser
                85                  90

<210> SEQ ID NO 7
<211> LENGTH: 58
<212> TYPE: PRT
<213> ORGANISM: Human herpesvirus 6A

<400> SEQUENCE: 7

Met Ser Ile Arg Leu Phe Ile Gly Phe Phe Tyr Thr Ala Tyr Ile Gly
1               5                   10                  15

Met Ala Ile Gly Phe Ile Cys Ser Ser Pro Asp Ala Glu Leu Phe Ser
                20                  25                  30

Glu Lys Ser Arg Met Ser Ser Ser Val Leu Leu Gly Cys Leu Leu Cys
            35                  40                  45

Cys Met Asp Trp Ser Ala Ala Val Pro Val
    50                  55

<210> SEQ ID NO 8
<211> LENGTH: 38
<212> TYPE: PRT
<213> ORGANISM: Human herpesvirus 6A

<400> SEQUENCE: 8

Phe Ile Cys Ser Ser Pro Asp Ala Glu Leu Phe Ser Glu Lys Ser Arg
1               5                   10                  15

Met Ser Ser Ser Val Leu Leu Gly Cys Leu Leu Cys Cys Met Asp Trp
                20                  25                  30

Ser Ala Ala Val Pro Val
            35

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9
ttggatcctt tatatgtagt tcccccgatg                                    30

<210> SEQ ID NO 10
<211> LENGTH: 48
<212> TYPE: DNA
<213> ORGANISM: Artificial
<220> FEATURE:
<223> OTHER INFORMATION: primer

<400> SEQUENCE: 10
tcgggatccc gtgatgatga tgacaaattt atatgtagtt cccccgat                48

<210> SEQ ID NO 11
<211> LENGTH: 45
<212> TYPE: DNA
<213> ORGANISM: Artificial
<220> FEATURE:
<223> OTHER INFORMATION: primer
```

```
<400> SEQUENCE: 11
tcgggatccc gtatcgaagg tcgtttata tgtagttccc ccgat              45

<210> SEQ ID NO 12
<211> LENGTH: 28
<212> TYPE: DNA
<213> ORGANISM: Artificial
<220> FEATURE:
<223> OTHER INFORMATION: primer

<400> SEQUENCE: 12
cttcgaattc tttcatgatt ctttgtct                                28

<210> SEQ ID NO 13
<211> LENGTH: 23
<212> TYPE: DNA
<213> ORGANISM: Artificial
<220> FEATURE:
<223> OTHER INFORMATION: primer

<400> SEQUENCE: 13
ccgggagctg catgtgtcag agg                                     23

<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14
aacgtattga agctatccca c                                       21

<210> SEQ ID NO 15
<211> LENGTH: 8
<212> TYPE: PRT
<213> ORGANISM: Artificial
<220> FEATURE:
<223> OTHER INFORMATION: N-terminal amino acid additions

<400> SEQUENCE: 15

Gly Ser Arg Asp Asp Asp Asp Lys
1               5

<210> SEQ ID NO 16
<211> LENGTH: 7
<212> TYPE: PRT
<213> ORGANISM: Artificial
<220> FEATURE:
<223> OTHER INFORMATION: N-terminal amino acid additions

<400> SEQUENCE: 16

Gly Ser Arg Ile Glu Gly Arg
1               5
```